US011948671B2

(12) United States Patent
Pryor et al.

(10) Patent No.: US 11,948,671 B2
(45) Date of Patent: Apr. 2, 2024

(54) INTELLIGENT ACCESSORIES FOR MEDICINE DISPENSING DEVICE

(71) Applicant: MEDTRONIC MINIMED INC., Northridge, CA (US)

(72) Inventors: Jack Pryor, San Diego, CA (US); Arnold Holmquist, San Diego, CA (US); Michael Mensinger, San Diego, CA (US); Sean Saint, San Diego, CA (US); Cory McCluskey, San Diego, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 301 days.

(21) Appl. No.: 16/846,810

(22) Filed: Apr. 13, 2020

(65) Prior Publication Data
US 2020/0327973 A1    Oct. 15, 2020

Related U.S. Application Data

(60) Provisional application No. 62/832,804, filed on Apr. 11, 2019.

(51) Int. Cl.
*G16H 20/17*    (2018.01)
*G16H 20/13*    (2018.01)
(Continued)

(52) U.S. Cl.
CPC .............. *G16H 20/17* (2018.01); *G16H 20/13* (2018.01); *G16H 40/67* (2018.01); *H04W 4/029* (2018.02)

(58) Field of Classification Search
CPC ........ G16H 20/13; G16H 20/17; G16H 40/63; G16H 40/67; H04W 4/029; H04W 4/80;
(Continued)

(56) References Cited

U.S. PATENT DOCUMENTS

| 4,498,904 A | 2/1985 | Turner et al. |
| 4,515,584 A | 5/1985 | Abe et al. |

(Continued)

FOREIGN PATENT DOCUMENTS

| EP | 0298067 | 4/1989 |
| EP | 513128 | 11/1992 |

(Continued)

OTHER PUBLICATIONS

Cision PR News Wire, "CompaNion Medical Announces Insights by InPen, the Future of MDI Reports", Jun. 20, 2018.
(Continued)

*Primary Examiner* — Shah M Rahman
(74) *Attorney, Agent, or Firm* — Carter, DeLuca & Farrell LLP

(57) ABSTRACT

Intelligent (smart) tracking accessories for a medicine dispensing device, such as an injection pen or pen device, are described. A smart tracking accessory in the form of a smart cap for a medicine dispensing device, such as an insulin pen, is configured to protect the needle of the dispensing device and the medicine contained therein when the device is not in use. The smart cap may detect the presence of the medicine dispensing device, detect an activation event such as removal from the medicine dispensing device, inform the user whether it is safe to administer a therapeutic dose of medicine, and log occurrence of the dosing event.

24 Claims, 14 Drawing Sheets

(51) Int. Cl.
*G16H 40/67* (2018.01)
*H04W 4/029* (2018.01)

(58) Field of Classification Search
CPC .......... A61B 5/683; A61B 2017/00477; A61B 2017/00486
See application file for complete search history.

(56) References Cited

U.S. PATENT DOCUMENTS

| | | | |
|---|---|---|---|
| 4,702,739 A * | 10/1987 | Milorad | A61M 5/3272 604/198 |
| 4,939,705 A * | 7/1990 | Hamilton | A61J 7/0436 368/10 |
| 4,950,216 A | 8/1990 | Weder | |
| 4,973,318 A | 11/1990 | Holm et al. | |
| 4,988,660 A | 1/1991 | Campbell | |
| 5,279,586 A | 1/1994 | Balkwill | |
| 5,626,566 A | 5/1997 | Petersen et al. | |
| 5,681,285 A | 10/1997 | Ford et al. | |
| 5,822,715 A | 10/1998 | Worthington et al. | |
| 5,925,021 A | 7/1999 | Castellano et al. | |
| 5,984,900 A | 11/1999 | Mikkelsen | |
| 5,993,421 A * | 11/1999 | Kriesel | A61M 5/1454 604/151 |
| 6,004,297 A | 12/1999 | Steenfeldt-Jensen et al. | |
| 6,042,571 A | 3/2000 | Hjertman et al. | |
| 6,235,004 B1 | 5/2001 | Steenfeldt-Jensen et al. | |
| 6,302,855 B1 | 10/2001 | Lav et al. | |
| 6,482,185 B1 | 11/2002 | Hartmann | |
| 6,817,986 B2 | 11/2004 | Slate et al. | |
| 7,133,329 B2 | 11/2006 | Skyggebjerg et al. | |
| 7,397,730 B2 | 7/2008 | Skyggebjerg et al. | |
| 7,591,801 B2 | 9/2009 | Brauker et al. | |
| 7,905,833 B2 | 3/2011 | Brister et al. | |
| 7,955,303 B2 | 6/2011 | Burren et al. | |
| 7,976,492 B2 | 7/2011 | Brauker et al. | |
| 8,052,655 B2 | 11/2011 | Moeller et al. | |
| 8,221,356 B2 | 7/2012 | Enggaard et al. | |
| 8,229,535 B2 | 7/2012 | Mensinger et al. | |
| 8,231,531 B2 | 7/2012 | Brister et al. | |
| RE43,834 E | 11/2012 | Steenfeldt-Jensen et al. | |
| 8,460,231 B2 | 6/2013 | Brauker et al. | |
| 8,565,848 B2 | 10/2013 | Brister et al. | |
| D694,252 S | 11/2013 | Helm | |
| 8,591,455 B2 | 11/2013 | Mensinger et al. | |
| 8,663,109 B2 | 3/2014 | Brister et al. | |
| 8,721,585 B2 | 5/2014 | Mensinger et al. | |
| 8,743,662 B2 | 6/2014 | Sjolund et al. | |
| 8,750,955 B2 | 6/2014 | Mensinger et al. | |
| 8,808,228 B2 | 8/2014 | Brister et al. | |
| 8,817,258 B2 | 8/2014 | Whalley et al. | |
| 8,821,452 B2 | 9/2014 | Dasbach et al. | |
| 8,882,722 B2 | 11/2014 | Bode et al. | |
| 8,882,741 B2 | 11/2014 | Brauker et al. | |
| 8,920,401 B2 | 12/2014 | Brauker et al. | |
| 8,926,585 B2 | 1/2015 | Brauker et al. | |
| D727,928 S | 4/2015 | Allison et al. | |
| 9,020,572 B2 | 4/2015 | Mensinger et al. | |
| 9,050,413 B2 | 6/2015 | Brauker et al. | |
| 9,089,650 B2 | 7/2015 | Nielsen et al. | |
| 9,101,723 B2 | 8/2015 | Larsen | |
| 9,108,006 B2 | 8/2015 | Jensen et al. | |
| D738,385 S | 9/2015 | Lim et al. | |
| 9,125,991 B2 | 9/2015 | Schabbach et al. | |
| 9,143,569 B2 | 9/2015 | Mensinger et al. | |
| 9,155,843 B2 | 10/2015 | Brauker et al. | |
| D747,333 S | 1/2016 | Supino et al. | |
| D748,101 S | 1/2016 | Bang et al. | |
| D748,126 S | 1/2016 | Sarukkai et al. | |
| 9,233,210 B2 | 1/2016 | Bock et al. | |
| D749,103 S | 2/2016 | Song | |
| 9,250,111 B2 | 2/2016 | Whalley et al. | |
| 9,255,830 B2 | 2/2016 | Whalley et al. | |
| D753,685 S | 4/2016 | Zimmerman et al. | |
| D754,689 S | 4/2016 | Lee | |
| D759,684 S | 6/2016 | Bijlani et al. | |
| D761,280 S | 7/2016 | Chung et al. | |
| D763,308 S | 8/2016 | Wang et al. | |
| D766,958 S | 9/2016 | Salazar Cardozo et al. | |
| 9,446,194 B2 | 9/2016 | Kamath et al. | |
| 9,483,620 B2 | 11/2016 | Reimer | |
| 9,526,838 B2 | 12/2016 | Baran et al. | |
| D777,760 S | 1/2017 | Zhao et al. | |
| 9,545,482 B2 | 1/2017 | Binier | |
| D781,890 S | 3/2017 | Gathman et al. | |
| 9,604,004 B2 | 3/2017 | Jakobsen | |
| D783,037 S | 4/2017 | Hariharan et al. | |
| D783,648 S | 4/2017 | Vazquez et al. | |
| D784,391 S | 4/2017 | Yuguchi et al. | |
| D785,025 S | 4/2017 | Zimmerman et al. | |
| 9,619,625 B2 | 4/2017 | Bengtsson | |
| 9,623,188 B2 | 4/2017 | Nielsen et al. | |
| D786,273 S | 5/2017 | Herman et al. | |
| 9,636,461 B2 | 5/2017 | Bengtsson et al. | |
| 9,636,464 B1 | 5/2017 | Binier | |
| 9,638,564 B2 | 5/2017 | Whalley et al. | |
| 9,642,968 B2 | 5/2017 | Whalley et al. | |
| 9,649,448 B2 | 5/2017 | Madsen | |
| 9,651,482 B2 | 5/2017 | Blei et al. | |
| 9,672,328 B2 | 6/2017 | Saint | |
| 9,675,761 B2 | 6/2017 | Hoeholt et al. | |
| D791,806 S | 7/2017 | Brewington et al. | |
| D794,047 S | 8/2017 | Gandhi et al. | |
| D795,900 S | 8/2017 | Bischoff et al. | |
| D795,919 S | 8/2017 | Bischoff et al. | |
| D795,927 S | 8/2017 | Bischoff et al. | |
| 9,721,176 B2 | 8/2017 | Prager | |
| 9,734,302 B2 | 8/2017 | Nielsen et al. | |
| 9,737,665 B2 | 8/2017 | Heumann et al. | |
| D797,760 S | 9/2017 | Tsujimura et al. | |
| D798,312 S | 9/2017 | Tsujimura et al. | |
| 9,750,882 B2 | 9/2017 | Blei et al. | |
| 9,750,886 B2 | 9/2017 | Plambech et al. | |
| 9,775,543 B2 | 10/2017 | Brister et al. | |
| 9,782,543 B2 | 10/2017 | Groeschke et al. | |
| 9,782,544 B2 | 10/2017 | Heumann et al. | |
| 9,789,260 B1 | 10/2017 | Binier | |
| 9,790,977 B2 | 10/2017 | Baran et al. | |
| D802,760 S | 11/2017 | Neby | |
| 9,833,576 B2 | 12/2017 | Windum et al. | |
| D808,986 S | 1/2018 | Dudey | |
| D809,544 S | 2/2018 | Ambielli | |
| D809,545 S | 2/2018 | Ban et al. | |
| D811,425 S | 2/2018 | Olsen et al. | |
| D815,127 S | 4/2018 | Phillips et al. | |
| D815,667 S | 4/2018 | Yeung | |
| 9,937,293 B2 | 4/2018 | Brauker et al. | |
| D819,043 S | 5/2018 | Yamaura et al. | |
| D820,297 S | 6/2018 | Gardner et al. | |
| 9,996,668 B2 | 6/2018 | Reihman et al. | |
| 10,016,565 B2 | 7/2018 | Nielsen et al. | |
| 10,043,093 B2 | 8/2018 | Allerdings et al. | |
| 10,071,205 B2 | 9/2018 | Blei et al. | |
| D831,049 S | 10/2018 | Agarwal et al. | |
| D831,684 S | 10/2018 | Ghosh | |
| D832,292 S | 10/2018 | Hu et al. | |
| 10,086,141 B2 | 10/2018 | Steel et al. | |
| 10,105,094 B2 | 10/2018 | Baran et al. | |
| 10,105,497 B2 | 10/2018 | Dreier et al. | |
| D832,870 S | 11/2018 | Hu | |
| D833,469 S | 11/2018 | Coleman et al. | |
| D834,710 S | 11/2018 | Michael | |
| 10,117,996 B2 | 11/2018 | Stefansen | |
| 10,117,999 B2 | 11/2018 | Andersen | |
| 10,133,948 B2 | 11/2018 | Hammen | |
| D835,118 S | 12/2018 | Lee et al. | |
| 10,155,090 B2 | 12/2018 | Larsen et al. | |
| 10,159,797 B2 | 12/2018 | Andersen et al. | |
| 10,159,798 B2 | 12/2018 | Blei et al. | |
| D837,807 S | 1/2019 | Baber et al. | |
| D838,734 S | 1/2019 | Kruse et al. | |
| 10,166,338 B2 | 1/2019 | Nielsen et al. | |
| 10,166,340 B2 | 1/2019 | Blei et al. | |

(56) References Cited

U.S. PATENT DOCUMENTS

| | | |
|---|---|---|
| 10,169,539 B2 | 1/2019 | Reihman et al. |
| 10,179,207 B2 | 1/2019 | Haupt |
| 10,183,119 B2 | 1/2019 | Andersen et al. |
| 10,183,120 B2 | 1/2019 | Sihlanick et al. |
| 10,190,901 B2 | 1/2019 | Whalley et al. |
| 10,195,351 B2 | 2/2019 | Allerdings et al. |
| 10,195,352 B2 | 2/2019 | Baran et al. |
| 10,195,355 B2 | 2/2019 | Allerdings et al. |
| D842,888 S | 3/2019 | Krainer et al. |
| D843,402 S | 3/2019 | Casse et al. |
| 10,231,903 B2 * | 3/2019 | Danopoulos ....... A61K 31/4458 |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 10,682,287 B2 * | 6/2020 | Davis .................... A61J 7/0053 |
| 11,571,165 B1 * | 2/2023 | Knas .................... A61B 5/4839 |
| 2003/0065536 A1 | 4/2003 | Hansen et al. |
| 2004/0039255 A1 | 2/2004 | Simonsen et al. |
| 2004/0135002 A1 * | 7/2004 | Beller ................. B05B 11/0038 239/103 |
| 2005/0038674 A1 | 2/2005 | Braig et al. |
| 2005/0043674 A1 * | 2/2005 | Blair ...................... G16H 20/13 604/66 |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0228057 A1 | 9/2008 | Graskov et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0292634 A1 | 11/2010 | Kircher, Jr. et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2013/0309637 A1 * | 11/2013 | Minvielle .......... G09B 19/0092 434/430 |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0023815 A1 * | 1/2014 | Steckler .................... G09F 3/14 428/42.1 |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0207048 A1 * | 7/2014 | DiPierro ................. A61P 13/02 604/20 |
| 2014/0207080 A1 | 7/2014 | Allerdings |
| 2014/0257065 A1 | 9/2014 | Walsh |
| 2014/0276531 A1 | 9/2014 | Walsh |
| 2014/0288494 A1 | 9/2014 | Brister et al. |
| 2014/0324020 A1 | 10/2014 | Stefansen |
| 2014/0371682 A1 | 12/2014 | Bengtsson et al. |
| 2015/0073337 A1 | 3/2015 | Saint et al. |
| 2015/0202375 A1 | 7/2015 | Schabbach et al. |
| 2015/0202377 A1 | 7/2015 | Haupt |
| 2015/0306304 A1 | 10/2015 | Schabbach et al. |
| 2015/0351683 A1 | 12/2015 | Brauker et al. |
| 2015/0356273 A1 | 12/2015 | Cave |
| 2015/0359965 A1 | 12/2015 | O'Connor et al. |
| 2016/0012205 A1 | 1/2016 | Saint |
| 2016/0015957 A1 * | 1/2016 | Tieck .................. A61M 5/5086 604/533 |
| 2016/0030673 A1 | 2/2016 | White et al. |
| 2016/0030679 A1 | 2/2016 | Nielsen et al. |
| 2016/0030680 A1 | 2/2016 | Veasey et al. |
| 2016/0030683 A1 | 2/2016 | Taylor |
| 2016/0038675 A1 | 2/2016 | Estes et al. |
| 2016/0047685 A1 | 2/2016 | Blei et al. |
| 2016/0051760 A1 | 2/2016 | Krusell et al. |
| 2016/0065799 A1 | 3/2016 | Haupt et al. |
| 2016/0066843 A1 | 3/2016 | Mensinger et al. |
| 2016/0081632 A1 | 3/2016 | Kamath et al. |
| 2016/0082192 A1 | 3/2016 | Veasey et al. |
| 2016/0101232 A1 | 4/2016 | Kamath et al. |
| 2016/0101234 A1 | 4/2016 | Bock et al. |
| 2016/0106927 A1 | 4/2016 | Moeller et al. |
| 2016/0235925 A1 | 8/2016 | Kuhn et al. |
| 2016/0263327 A1 | 9/2016 | Radmer et al. |
| 2016/0287804 A1 | 10/2016 | Madsen et al. |
| 2016/0287807 A1 | 10/2016 | Madsen et al. |
| 2017/0014310 A1 * | 1/2017 | Hyun .................. A61J 15/0026 |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0132392 A1 | 5/2017 | Gerken |
| 2017/0138769 A1 | 5/2017 | Jones et al. |
| 2017/0151390 A1 | 6/2017 | Muller-pathle |
| 2017/0182258 A1 | 6/2017 | Michael |
| 2017/0185283 A1 | 6/2017 | Bhavaraju et al. |
| 2017/0185284 A1 | 6/2017 | Bhavaraju et al. |
| 2017/0189616 A1 | 7/2017 | Bengtsson et al. |
| 2017/0189625 A1 | 7/2017 | Cirillo et al. |
| 2017/0219486 A1 | 8/2017 | Blei et al. |
| 2017/0224922 A1 | 8/2017 | Lepple-wienhues |
| 2017/0224927 A1 | 8/2017 | Windum et al. |
| 2017/0232203 A1 | 8/2017 | Krusell |

(56) References Cited

U.S. PATENT DOCUMENTS

| | | | |
|---|---|---|---|
| 2017/0232204 A1* | 8/2017 | Knapp | A61M 5/347 604/66 |
| 2017/0235919 A1 | 8/2017 | Bauss et al. | |
| 2017/0235920 A1 | 8/2017 | Bauss et al. | |
| 2017/0266389 A1 | 9/2017 | Mcloughlin et al. | |
| 2017/0270276 A1 | 9/2017 | Saint et al. | |
| 2017/0270829 A1 | 9/2017 | Bauss | |
| 2017/0286194 A1 | 10/2017 | Morris et al. | |
| 2017/0286614 A1 | 10/2017 | Morris et al. | |
| 2017/0304538 A1 | 10/2017 | Renstad et al. | |
| 2017/0304541 A1 | 10/2017 | Bauss et al. | |
| 2017/0304552 A1 | 10/2017 | Prager | |
| 2017/0312446 A1 | 11/2017 | Kunz et al. | |
| 2017/0316178 A1 | 11/2017 | Riedel et al. | |
| 2017/0338864 A1 | 11/2017 | Rolsted et al. | |
| 2017/0340808 A1 | 11/2017 | Andersen et al. | |
| 2017/0340826 A1 | 11/2017 | Draper | |
| 2017/0366617 A1 | 12/2017 | Mensinger et al. | |
| 2017/0367627 A1 | 12/2017 | Brister et al. | |
| 2017/0368263 A1 | 12/2017 | Ploch | |
| 2017/0368265 A1 | 12/2017 | Groeschke et al. | |
| 2018/0001027 A1 | 1/2018 | Klemm et al. | |
| 2018/0008773 A1 | 1/2018 | Hautaviita et al. | |
| 2018/0008778 A1 | 1/2018 | Erbstein | |
| 2018/0008779 A1 | 1/2018 | Hautaviita et al. | |
| 2018/0028759 A1 | 2/2018 | Riedel et al. | |
| 2018/0028760 A1 | 2/2018 | Gugl et al. | |
| 2018/0036484 A1 | 2/2018 | Andersen | |
| 2018/0043104 A1 | 2/2018 | Mueller-Pathle | |
| 2018/0050157 A1 | 2/2018 | Whalley et al. | |
| 2018/0060517 A1* | 3/2018 | Bagwell | G16H 20/60 |
| 2018/0064879 A1 | 3/2018 | Säll et al. | |
| 2018/0085532 A1 | 3/2018 | Desborough et al. | |
| 2018/0099084 A1 | 4/2018 | Schabbach et al. | |
| 2018/0154086 A1 | 6/2018 | Toporek et al. | |
| 2018/0161505 A1 | 6/2018 | Prager | |
| 2018/0185587 A1 | 7/2018 | Brauker et al. | |
| 2018/0200451 A1 | 7/2018 | Shekalim | |
| 2018/0221582 A1 | 8/2018 | Klemm et al. | |
| 2018/0224315 A1 | 8/2018 | Schabbacha et al. | |
| 2018/0228977 A1 | 8/2018 | Schabbach et al. | |
| 2018/0236172 A1 | 8/2018 | Schabbach et al. | |
| 2018/0236185 A1 | 8/2018 | Säll et al. | |
| 2018/0243504 A1 | 8/2018 | Scott et al. | |
| 2018/0268236 A1 | 9/2018 | Klemm | |
| 2018/0272072 A1 | 9/2018 | Radmer et al. | |
| 2018/0296767 A1 | 10/2018 | Säll | |
| 2018/0303417 A1 | 10/2018 | Mensinger et al. | |
| 2018/0304028 A1 | 10/2018 | Riedel | |
| 2018/0326164 A1 | 11/2018 | Bauss et al. | |
| 2018/0339113 A1 | 11/2018 | Wendland et al. | |
| 2018/0341826 A1 | 11/2018 | Allerdings et al. | |
| 2018/0353694 A1 | 12/2018 | Riedel et al. | |
| 2018/0353698 A1 | 12/2018 | Saint et al. | |
| 2018/0353699 A1 | 12/2018 | Helmer et al. | |
| 2018/0353700 A1 | 12/2018 | Säll et al. | |
| 2018/0361067 A1 | 12/2018 | Säll et al. | |
| 2018/0361076 A1 | 12/2018 | Klemm et al. | |
| 2018/0361082 A1 | 12/2018 | Säll et al. | |
| 2018/0369488 A1 | 12/2018 | Carlsson et al. | |
| 2018/0369490 A1 | 12/2018 | Rehbein et al. | |
| 2019/0001060 A1 | 1/2019 | Gylleby et al. | |
| 2019/0001069 A1 | 1/2019 | Carlsson et al. | |
| 2019/0009032 A1 | 1/2019 | Hautaviita et al. | |
| 2019/0015020 A1 | 1/2019 | Brister et al. | |
| 2019/0022320 A1 | 1/2019 | Carlsson et al. | |
| 2019/0029590 A1 | 1/2019 | Baran et al. | |
| 2019/0030250 A1 | 1/2019 | Steel et al. | |
| 2019/0035500 A1 | 1/2019 | Saint et al. | |
| 2019/0132801 A1 | 5/2019 | Kamath et al. | |
| 2019/0173885 A1 | 6/2019 | Kamath et al. | |
| 2019/0175833 A1* | 6/2019 | Sjolund | A61B 5/14532 |
| 2019/0183434 A1* | 6/2019 | Sjolund | A61B 5/14532 |
| 2019/0184092 A1* | 6/2019 | Sjolund | A61M 5/3202 |
| 2019/0184093 A1* | 6/2019 | Sjolund | A61B 5/7435 |
| 2019/0184094 A1* | 6/2019 | Sjolund | A61B 5/7405 |
| 2019/0184108 A1* | 6/2019 | Sjolund | A61B 5/14532 |
| 2019/0184109 A1* | 6/2019 | Sjolund | A61B 5/14532 |
| 2019/0184111 A1* | 6/2019 | Sjolund | A61M 5/3202 |
| 2019/0125224 A1 | 8/2019 | Kamath et al. | |
| 2019/0298920 A1* | 10/2019 | Haider | A61M 5/24 |
| 2020/0010224 A1* | 1/2020 | Koike | B65B 35/14 |
| 2020/0129743 A1* | 4/2020 | Perez | G01F 13/00 |
| 2020/0261656 A1* | 8/2020 | Helmer | A61M 5/31563 |
| 2020/0353175 A1* | 11/2020 | Helmer | A61M 5/3155 |
| 2021/0177328 A1* | 6/2021 | Helmer | A61B 5/18 |

FOREIGN PATENT DOCUMENTS

| | | |
|---|---|---|
| EP | 927057 | 7/1999 |
| EP | 2572740 | 3/2013 |
| WO | 9638190 | 12/1996 |
| WO | 2010052275 | 5/2010 |
| WO | 2011041007 | 4/2011 |
| WO | 2012046199 | 4/2012 |
| WO | 2013053695 | 4/2013 |
| WO | 2014029621 A1 | 2/2014 |
| WO | 2014128157 | 8/2014 |
| WO | 2015047870 | 4/2015 |
| WO | 2015169814 | 11/2015 |
| WO | 2015185686 | 12/2015 |
| WO | 2016071912 | 5/2016 |
| WO | 2017132577 | 3/2018 |

OTHER PUBLICATIONS

Copenheaver, B. R., Authorized Officer, ISA/US, International Search Report and Written Opinion, International Application No. PCT/US2014/056336, dated Dec. 31, 2014, 10 pages.
EPO, Extended European Search Report for European Patent Application No. 14849422.2, dated May 4, 2017, 11 pages.
EPO, Extended European Search Report for European Patent Application No. 17745019.4, dated Aug. 6, 2019, 9 pages.
ISA, International Search Report and Written Opinion for PCT Application No. PCT/US2018/036768; dated Aug. 31, 2018, 10 pages.
ISA, International Search Report and Written Opinion for PCT Application No. PCT/US2017/15452, dated May 23, 2017, 14 pages.
ISA, International Search Report and Written Opinion for PCT Application No. PCT/US2018/55646, dated Feb. 6, 2019, 15 pages.
ISA, International Search Report, International Application No. PCT/US15/40069, dated Dec. 22, 2015, 13 pages.
ISA, Invitation to Pay Additional Fees and Partial Search Report, International Application No. PCT/US15/40069, dated Oct. 1, 2015, 2 pages.

* cited by examiner

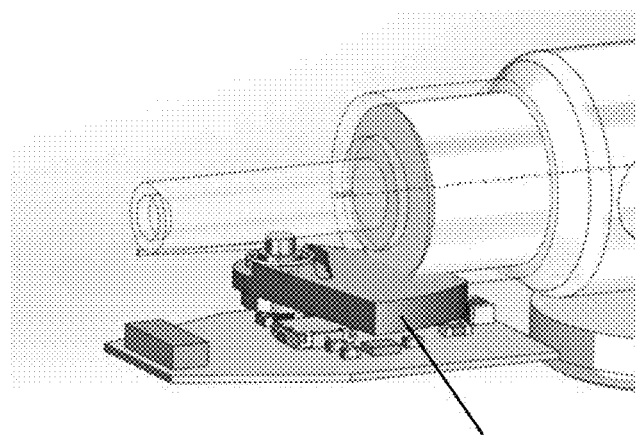
Fig. 19
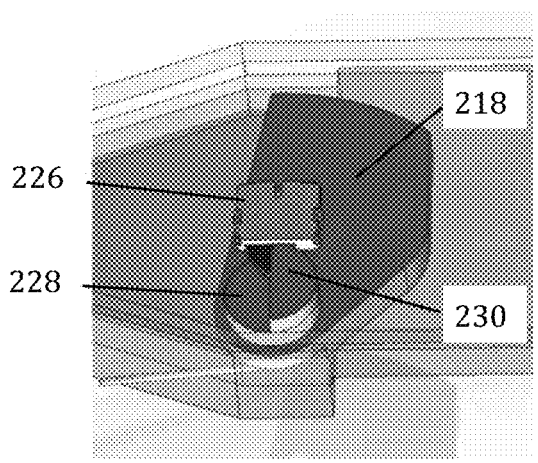　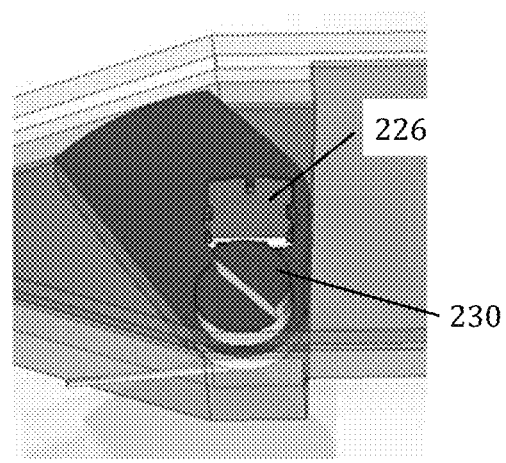
Fig. 20　　　　　　　Fig. 21

Example Embodiment 2: Confirm dose not yet taken, and communicate new doses

Example Embodiment 3: Communicate new doses and check for updates periodically

INTELLIGENT ACCESSORIES FOR MEDICINE DISPENSING DEVICE

CROSS-REFERENCES TO RELATED APPLICATIONS

This patent document claims priorities to and benefits of U.S. Provisional Patent Application No. 62/832,804, entitled "INTELLIGENT ACCESSORIES FOR MEDICINE INJECTION DEVICE" and filed on Apr. 11, 2019. The entire content of the aforementioned patent application is incorporated by reference as part of the disclosure of this patent document for all purposes.

TECHNICAL FIELD

The present disclosure relates to medicine administering and tracking systems, devices, and methods.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

SUMMARY

The present disclosure addresses the shortcomings of the prior art by describing intelligent (smart) tracking accessories for a medicine dispensing device, such as an injection pen or pen device. Moreover, the intelligent tracking accessories disclosed herein may be configured for use with many medicine dispensing devices, and many if not all of the medicine injection devices currently on the market.

According to one example embodiment, smart tracking accessory in the form of a smart cap for a medicine dispensing device, such as an insulin pen, is configured to protect the needle of the dispensing device (and the medicine contained therein) when the device is not in use. The smart cap may also indicate when the needle has been moved to an injection position to allow the medicine to be expelled from the dispensing device, with data associated with the dispensing of the medicine transferred to a companion computing device (e.g., smartphone) in communication with the medicine dispensing device. In some embodiments, the smart cap includes a switch that detects the presence of the medicine container portion of the dispensing device or of the external body. In various implementations, the smart cap accessory can be independent of the dispensing device and supplied separately from the dispensing device to replace the dispensing device's original cap.

In some implementations, the smart tracking accessory may be passively activated by the user interacting with the dispensing device, such as by picking up the dispensing device, removing the cap of the dispensing device, selecting a dose size of the dispensing device, and/or depressing a button to administer the dose by the dispensing device. By activating upon user interaction, the smart tracking accessory can maintain a record of when the dispensing device was used and may also display relevant information to the user about dosing requirements or history. By avoiding the need for manual user input (such a button press, or data entry in an app), the smart tracking accessory simplifies the user experience and obtains objective information about use of the device, unaffected by the user's willingness or remembering to manually log the dose. In addition to an activation means, the smart tracking accessory may include a real-time clock, a wireless data connection (such as a Bluetooth link to a smartphone), and various forms of user output, e.g., such as a light, LED, electronic ink (e-ink) display, alphanumeric display, graphical screen, speaker, piezoelectric beeper, vibration motor, or similar.

The smart cap protects the drug and needle when not in use. The switch can indicate when the cap is installed and removed from the dispensing device. In some embodiments, for example, the switch can include a mechanical contact switch, an optical switch, an inductive sensor, a hall-effect sensor built into the cap to detect the presence or absence of the dispensing device. The switch may detect the presence of the drug container portion of the dispensing device, or of the external body.

While pen injectors are made in various sizes and shapes, the needle interface at the tip is standardized, so the switch may be situated to detect the presence of the needle interface, minimizing variation of detection across devices and manufacturers. Needle hubs (installed onto the needle interface) are typically thin and similarly sized, so the same switch may easily sense the presence of the needle interface with or without a needle installed. Further, the accessory may detect whether a needle is installed based on the additional hub thickness over the threads, or the presence of the metal needle or the needle cover, and transmit this information to the smart device for tracking the use of needles or educating the user on proper storage of the device with no needle installed.

As dispensing devices come in different geometries from different manufacturers, the smart cap can be adaptable to these variations. One method of accommodating multiple dispensing device is to manufacture multiple variations of the smart cap that have size and retention features designed specifically for a particular dispensing device.

Another approach is to provide a single "smart" module and multiple adapters to the user and allow them to install the module in the appropriate adapter to fit onto their desired dispensing device. The module would attach securely for use, but would be detachable (e.g., by unsnapping a retention snap) for use with a different adapter that fits a different pen in case the user changes devices or installs the incorrect adapter.

In some embodiments, the disclosed smart cap is configured to provide a universal-fit cap that grips any dispensing device within a particular diameter and length range. Since snaps are different on different devices, one example method of retention is friction, with the cap applying inward radial force against the dispensing device to retain it in place reliably across a range of dispensing device sizes. This grip may take the form of a compliant elastomer that conforms to the particular dispensing device's size and shape. It may also take the form of spring-loaded or elastically deformable arms that expand as needed to allow different sized dispensing devices to fit.

While injector pens are nonstandard, pen needles are standardized with a defined thread geometry (exposed when no needle is installed) and a typical needle hub geometry that fits over the standard threads. A universal-fit smart cap can utilize this standard geometry to attach to, whether via friction, latch mechanism, or engagement with the threads. This needle feature is guaranteed to be similar across devices and manufacturers, so it provides a simpler attachment point for a universal-fit.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIGS. 17-21 are perspective cutaway views of an example switching mechanism forming part of the intelligent tracking accessory of FIG. 15;

DETAILED DESCRIPTION

Figure 1:
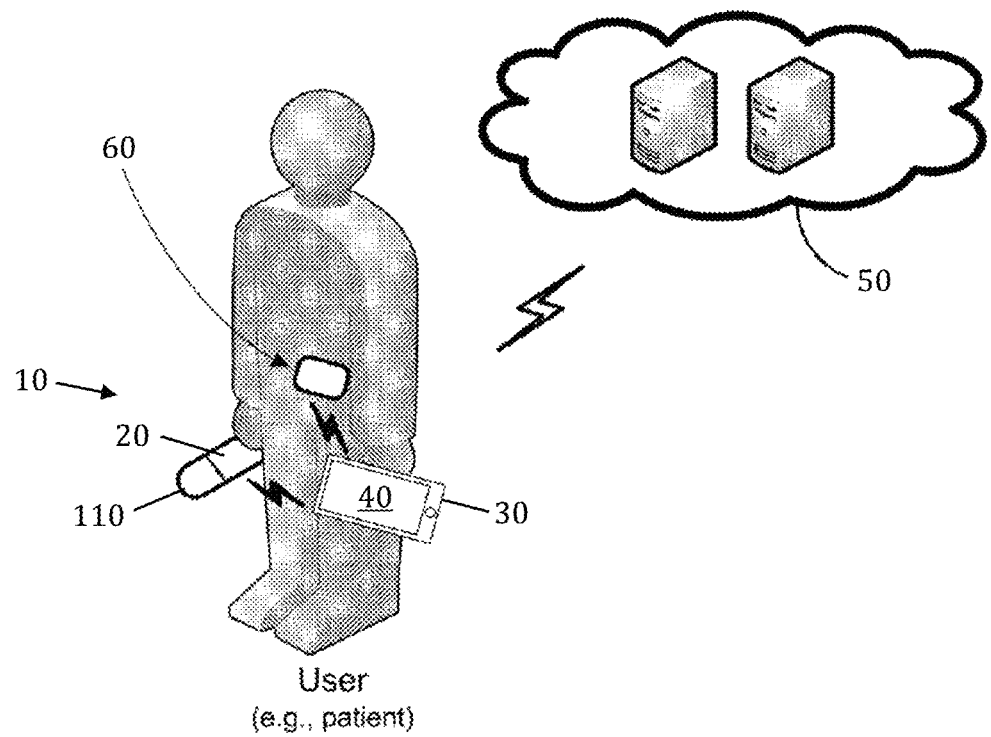
FIG. 1 is a block diagram representing an example of an intelligent medicine administering system according to one embodiment of the disclosure.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The intelligent accessories for medicine dispensing device and related methods disclosed herein boast a variety of features and components that warrant patent protection, both individually and in combination.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Because of this, physicians are unable to be certain when and how often the injections were taken, impeding their ability to educate the user most effectively. Additionally, without objective records of the doses taken, therapy cannot be reliably updated—whether manually by a physician or automatically by a software system—because it may be unclear whether patient outcomes were due to properly taken medication or missed doses. Additionally, patients may forget to take a dose or forget whether they have taken their scheduled dose, and may benefit from reminders and memory aids to improve compliance and prevent double-dosing.

Some infusion pumps and smart pens address these shortcomings, but may not be compatible with particular drugs or may not be cost-effective. Instead, it may be more practical to use a "smart" tracking accessory to an existing drug injection method.

Disclosed herein are intelligent (smart) tracking accessories (or "smart accessories") for a medicine dispensing device, such as an insulin pen injection device. In some example embodiments, the intelligent accessories may include one or more of a smart cap, dock, case, or other device attachable to and interactive with a medicine dispensing device. The present disclosure describes the various features of the smart accessories primarily through an example embodiment of a smart cap 110 configured to replace a regular cap provided with a standard dispensing device.

In some implementations, one or more of the smart tracking accessories may be configured for use with an intelligent medicine administering system 10, illustrated by way of example in FIG. 1. By way of example, the intelligent medicine administering system 10 includes a medicine dispensing device or pen device 20 (which may be a smart pen device or a standard pen device equipped with a smart cap 110) in wireless communication with a mobile computing and communication device 30 of a patient user, also referred to as the user's companion device. The pen device 20 is operable to select, set and/or dispense a dose of the medicine for dispensing. In some implementations, the companion device 30 comprises a smart phone, tablet, and/or wearable computing device, such as a smart watch, smart glasses, etc. In some implementations, the companion device 30 is in communication with other computing devices, such as a laptop and/or desktop computer, a smart television, or network-based server computer. The companion device 30 includes a health management software application or "app" 40 configured to send instructions to and receive data from associated devices and accessories of the intelligent medicine administering system 10, and also communicate useful information to a user through a user interface.

In some embodiments, the system 10 includes a data processing system 50 in communication with the companion device 30, the pen device 20, and/or an intelligent accessory such as a smart cap 110. The data processing system 50 can include one or more computing devices in a computer system or communication network accessible via the Internet (also referred to as "the cloud"), e.g., including servers and/or databases in the cloud.

The health management app 40 may be paired with the pen device 20 (e.g., if a smart pen device), the smart cap 110, and/or other intelligent accessories. In some implementations, the pairing (also referred to as bonding) of the companion device 30 to the pen device 20 indicates to the health management application 40 that the user is ready to use all features of the application, which can augment performance and provide important features to the intelligent medicine administering system 10. Thus, in some implementations the act of pairing (bonding) therefore enables the full functionality of the health management app 40. For example, in some cases the pairing may enable the entire app, in which at least a portion of the health management app 40 may be disabled without the specialized pairing; whereas in other cases, the pairing may enable certain features of the health management app 40, which otherwise provides some limited features without the specialized pairing. In some implementations, the act of pairing the companion device 30 to the smart cap 110 enables wireless communication and data transfer between the smart cap 110 and companion device 30 and health management app 40.

In some implementations, for example, the health management app 40 can monitor and/or control functionalities of the pen device 10 and/or smart cap 110 and provide a dose calculator, dose timing instruction, and/or decision support modules that can calculate and/or recommend a dose of the medicine for the patient user to administer using the pen device 20.

The companion device 30 can be used to obtain, process and/or display contextual data that can be used to relate to the patient user's health condition, including the condition for which the pen device 20 is used to treat. In an illustrative example, the companion device 30 is operable to track the patient user's location; the patient user's physical activity including step count, movement distance and/or intensity, estimated calories burned, and/or activity duration; and/or the patient user's interaction pattern with the companion device 30. In some implementations, the app 40 can aggregate and process the contextual data to generate decision support outputs to guide and aid the patient user in using the pen device 20 and/or smart cap 110 and/or managing their behavior to promote better health outcomes in treating his/her health condition.

In some embodiments, for example, the system 10 can optionally include a sensor device 60 to monitor one or more health metrics of the patient user. Examples of health metric data monitored by the sensor device 60 include analytes, such as glucose, heart rate, blood pressure, user movement, or other. In some implementations, the sensor device 60 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 30, which processes, stores and displays the continuous glucose values for the patient user.

The health management app 40 of the companion device 30 provides a user interface to allow the user to manage his/her health-related data. In some implementations, for example, the health management app 40 can be configured to control some functionalities of the pen device 20, smart cap 110, and/or additional intelligent accessories. In some implementations, for example, the health management app 40 provides an interactive user interface to allow a user to manage settings of the pen device 20, companion device 30 (e.g., smart phone, tablet, or wearable computing device), and/or smart accessories such as a smart cap 110 that can affect the functionality of the system 10. In implementations, for example, the companion device 30 is an independent portable device that the user may carry on his/her person. In example embodiments of the independent portable companion device 30, the companion device 30 includes a data processing unit, wireless communication unit to allow the device to communicate with the pen device 20, data processing system 50, sensor device 60, and/or smart cap 110 (and/or additional intelligent accessories), and a display unit.

Figure 2:
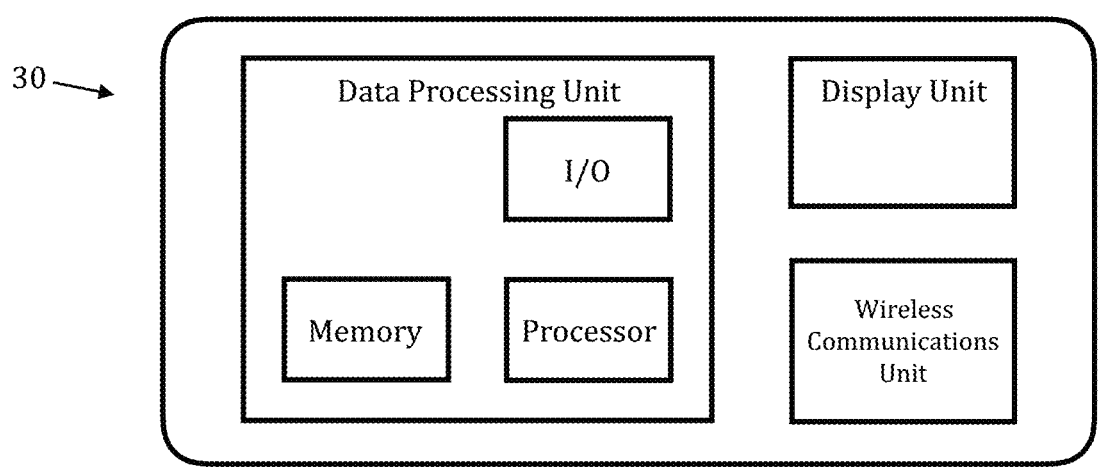
FIG. 2 is a block diagram representing an example of a companion device forming part of the intelligent medicine administering system of FIG. 1.
Figure 3:
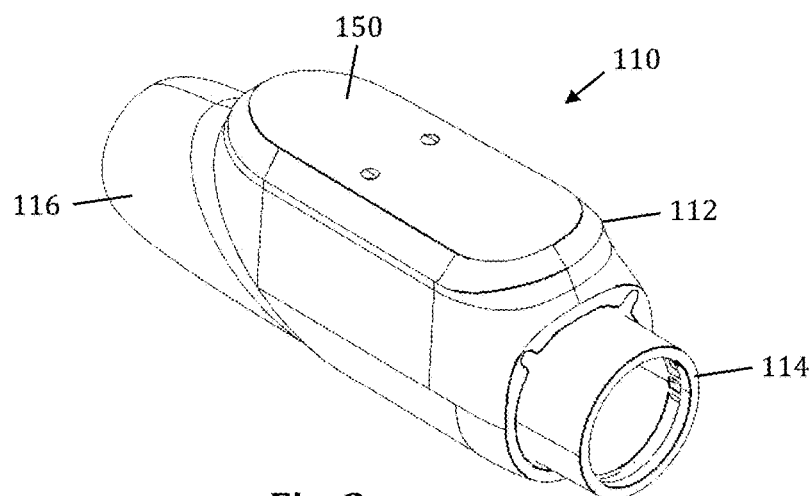
FIG. 3 is a perspective view of an example of an intelligent tracking accessory forming part of the intelligent medicine administering system of FIG. 1.
Figure 4:
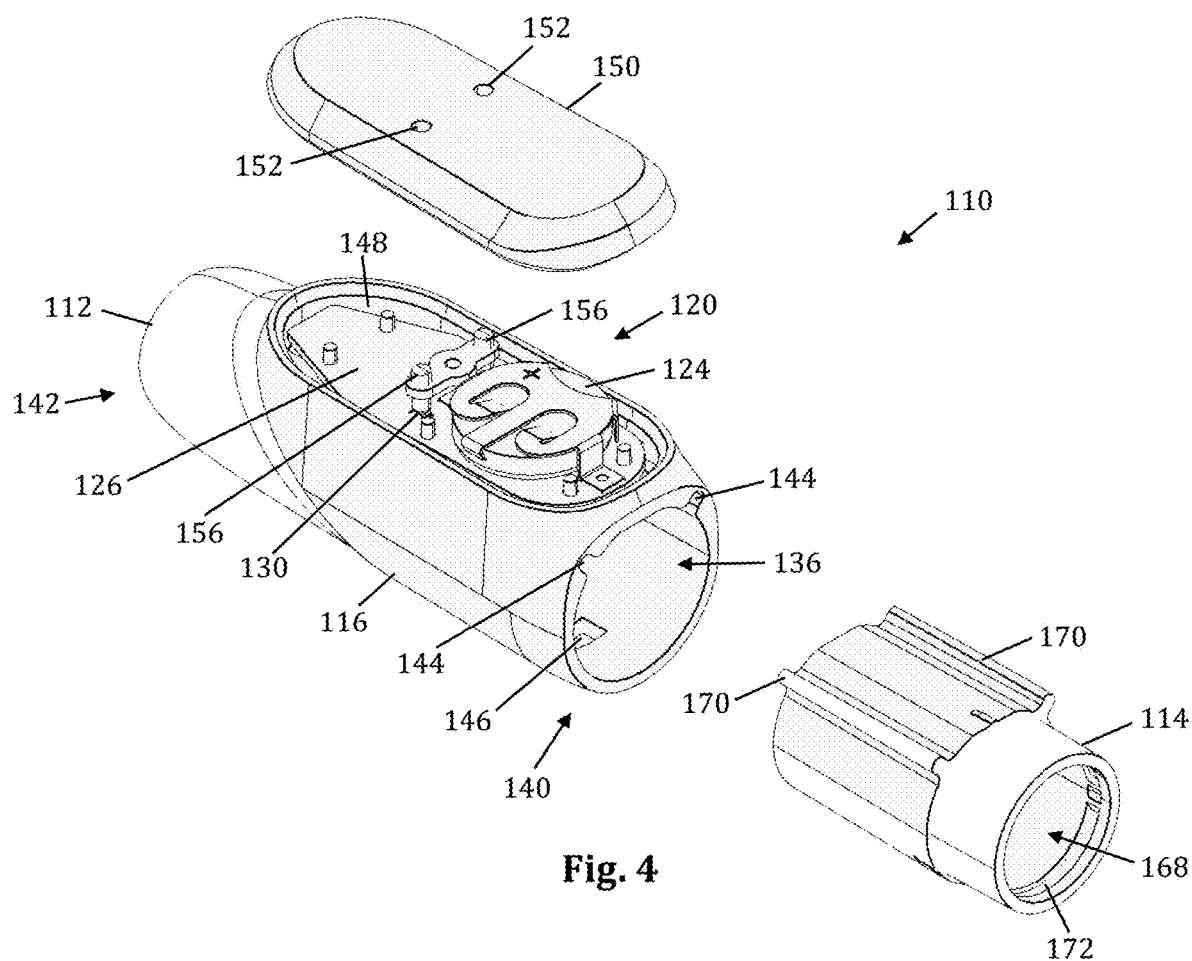
FIG. 4 is a partially exploded perspective view of the intelligent tracking accessory of FIG. 3.
Figure 5:
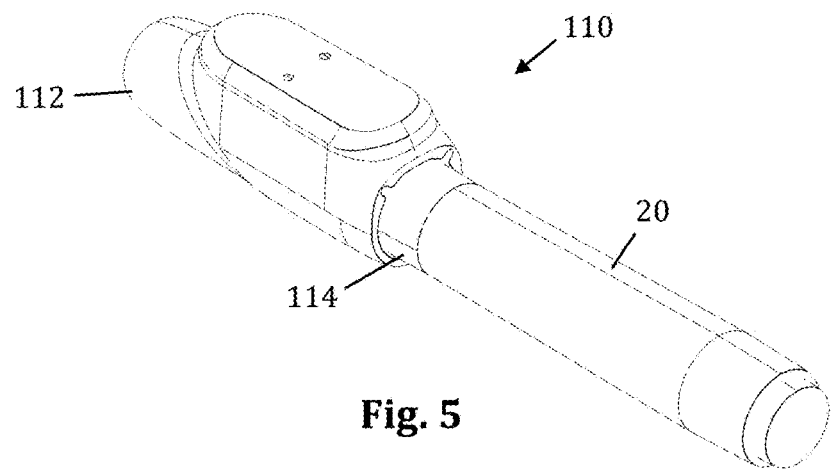
FIG. 5 is a perspective view of the intelligent tracking accessory of FIG. 3 coupled with a medicine dispensing device according to one embodiment.
Figure 6:
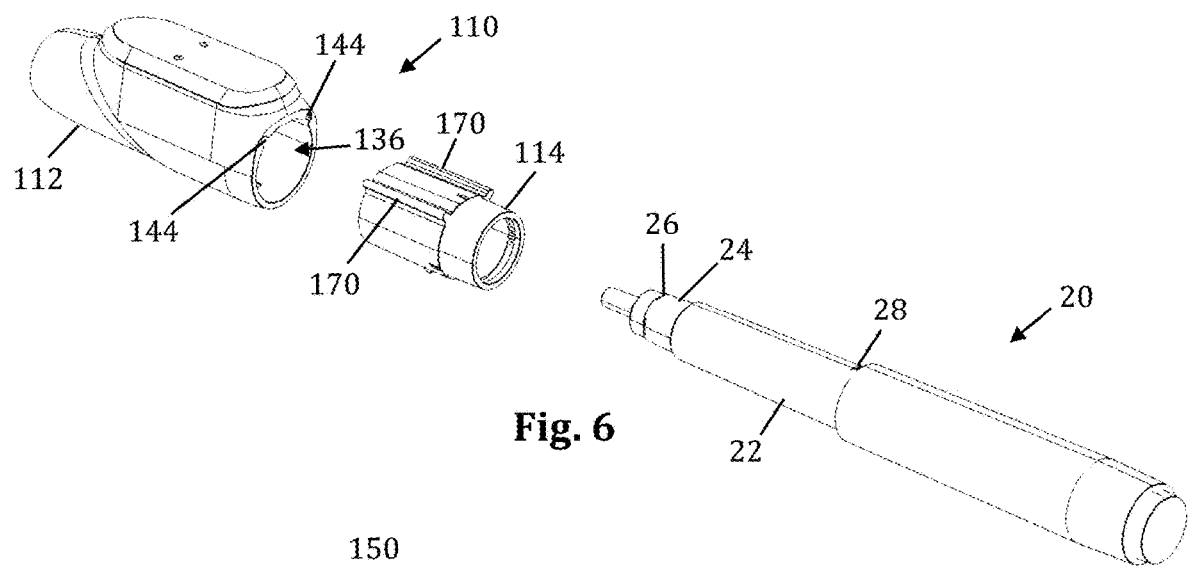
FIG. 6 is a partially exploded view of the intelligent tracking accessory and medicine dispensing device combination of FIG. 5.
Figure 7:
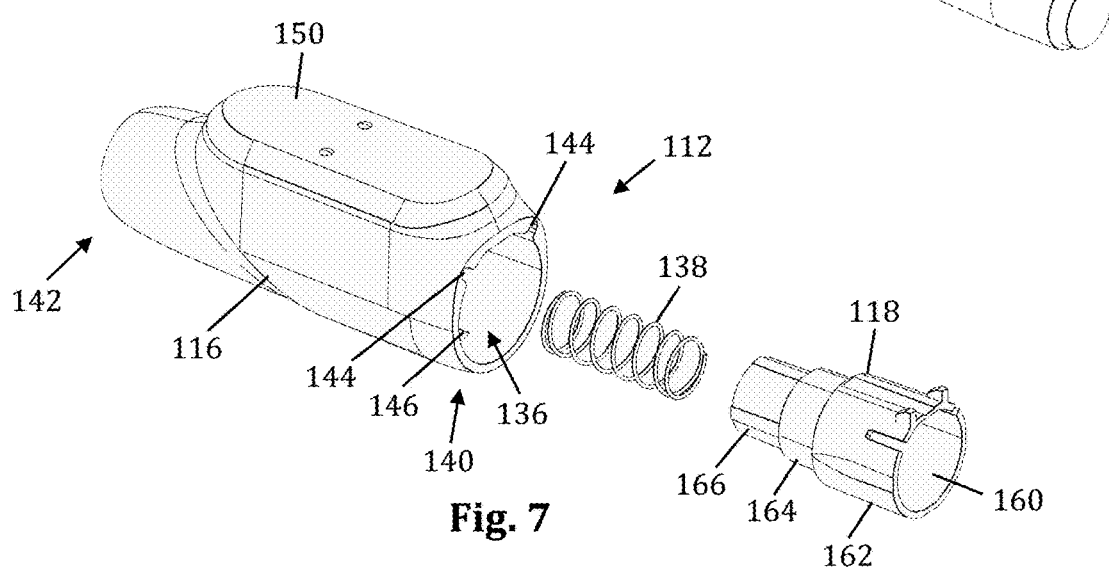
FIG. 7 is a partially exploded perspective view of a smart cap forming part of the intelligent tracking accessory of FIG. 3.
Figure 8:
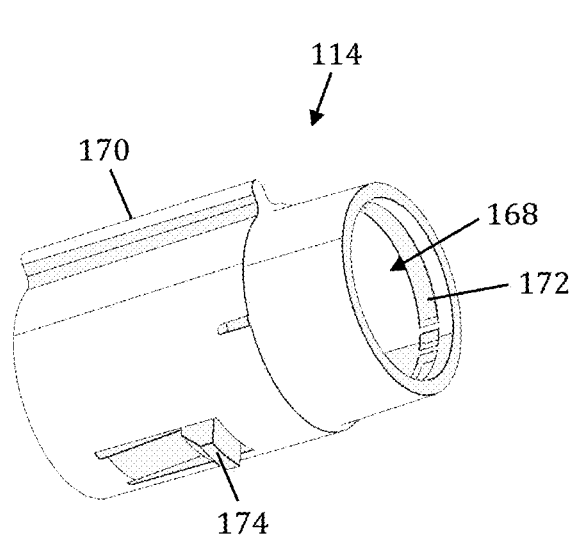
FIG. 8 is a perspective view of a coupler adapter forming part of the intelligent tracking accessory of FIG. 3.
Figure 9:
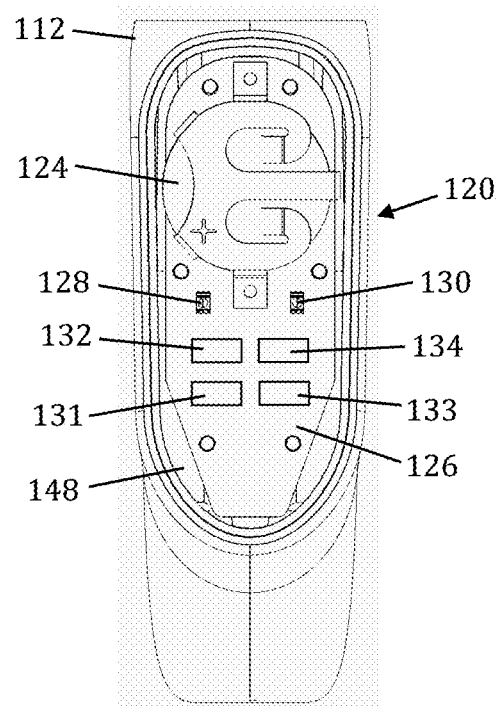
FIG. 9 is a top plan view of the smart cap of FIG. 7 with a top cover removed.
Figure 10:
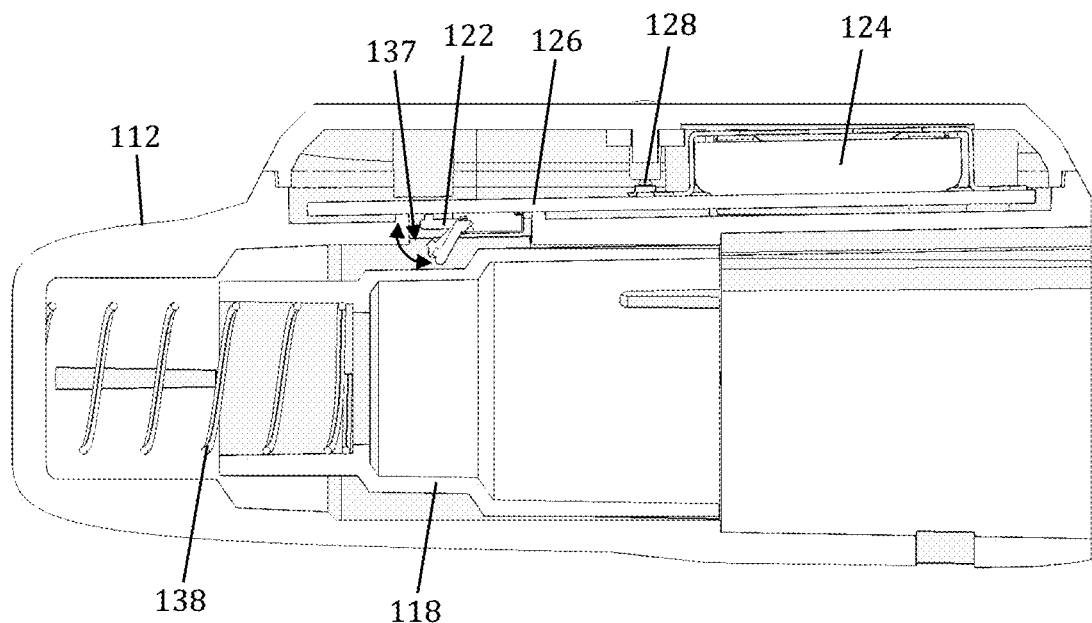
FIG. 10 is a side sectional view of the smart cap of FIG. 7.

FIG. 2 shows a block diagram of an example embodiment of the companion device 30 of the intelligent medicine administering system 10. The data processing unit of the companion device 30 includes a processor to process data, a memory in communication with the processor to store data, and an input/output unit (I/O) to interface the processor and/or memory to other modules, units or devices of the companion device 30 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device or accessory. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 20 and/or smart cap 110, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoper-ability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 30 or an external device. For example, a display unit of the companion device 30 can be configured to be in data communication with the data processing unit, e.g., via the I/O, to provide a visual display, an audio display, interactive touch-screen display, and/or other sensory display that produces the user interface of the health management application 40. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

Example embodiments and implementations of the disclosed intelligent medicine administering system 10, including the health management app 40 operable on a companion device 30 able to communicate with a medical device (e.g., medicine dispensing device such as a pen device 20 and/or smart cap 110), are described. Some examples of features of an intelligent medicine administering system 10 that can be used with the example methods, devices and systems for providing a prescription-regulated software controls on the system are described in U.S. Pat. No. 9,672,328 B2, entitled "Medicine Administering System Including Injection Pen and Companion Device," the entire content of which is incorporated by reference into this disclosure for all purposes.

While the disclosed embodiments described herein are primarily based on diabetes management systems and methods involving an insulin pen (e.g., configured to dispense liquid medication), health management app associated with the insulin pen, and/or smart accessories to facilitate understanding of the underlying concepts, it is understood that the disclosed embodiments can also include treatment of other health conditions using other medications by the pen device or alternative medicine container, health management app, smart accessories, and/or monitoring of other analytes by sensor devices. For example, the disclosed embodiments may include treatment of other health conditions using oral medications (e.g., pills) contained in a sealable container with a detachable lid to enable a user to retrieve a dose of the oral medication when needed.

FIGS. 3-10 illustrate an example of a smart tracking accessory in the form of a smart cap 110 configured to interact with a medicine injection device or pen device 20 according to one embodiment of the disclosure. The smart cap 110 may be configured in communication with the patient user's companion device 30, e.g., such as the user's smart phone, tablet, and/or wearable computing device, such as a smart watch, smart glasses, etc. and/or a user's laptop and/or desktop computer, a smart television, or network-based server computer. By way of example, the smart cap 110 comprises a cap unit 112 and a coupler adapter 114. The cap unit 112 includes a housing 116 and a spring-loaded slider 118, which together with the coupler adapter 114 are configured to receive and engage the medicine dispensing device 20. The cap unit 112 further includes a smart module 120 that comprises an activation mechanism (e.g., detection switch 122), a battery 124, a printed circuit board assembly or PCBA 126, user output in the form of first and second visual indicators (e.g., LED lights) 128, 130, a processor 131, a real-time clock 132, a storage module 133, a communications module 134 for wireless data transfer (such as a Bluetooth link to a companion device 30), and/or various forms of additional user output, e.g., such as an electronic ink (e-ink) display, alphanumeric display, graphical screen, speaker, piezoelectric beeper, vibration motor, or similar. By way of example, the medicine dispensing device 20 may comprise a pen injector device such as any commonly known in the art that comprises a medicine cartridge 22, a threaded needle interface 24, and a needle hub 26.

By way of example, when a dosing event (e.g., an amount of fluid is dispensed from the pen device 20) occurs, a time stamp associated with the dosing event is recorded by the processing unit 131 of the smart cap 110 (e.g., stored in the storage module 133 of the smart cap 110). For example, the time stamp may be the current time (provided by real-time clock 132) or a time where a count-up timer is used. When the dose information is eventually transmitted to the health management app 40 of the companion device 30, the time stamp and/or a time-since-dose parameter may be transmitted by the smart cap 110 and received by the companion device 30 and stored in the memory of the data processing unit of the companion device 30. In some implementations, for example, the time of the dose can be determined without the pen device 20 having to know the current time. This can simplify operation and setup of the pen device 20. In some implementations, for example, a user time is initialized on the smart cap 110 from the companion device 30, in which the user time is used for dose time tracking. Using the system 10, the health management app 40 can know the time of the dose relative to the current time. Once the companion device 30 receives the dose related information (e.g., which can include the time information and dose setting and/or dispensing information, and other information from the smart cap 110 related to the dosing event), the companion device 30 stores the dose related information in memory, e.g., which can include among a list of doses or dosing events.

By way of example, the housing 116 may include a generally cylindrical inner cavity or lumen 136 configured to receive the coupler adapter 114, slider 116, spring 138, and at least a portion of the medicine dispensing device 20 axially therein. The housing 116 of the present example has an open proximal end 140 to enable passage of the coupler adapter 114 and medicine dispensing device 20 into the interior cavity 136, and a closed distal end 142 to provide protection to the needle portion of the medicine dispensing device 20 while the smart cap 110 is coupled with the medicine dispensing device 20. The housing 116 of the present example further includes one or more alignment features 144 configured to mate with complementary alignment features 170 of the coupler adapter 114, and an aperture or recess 146 configured to engage the cantilever locking mechanism 174 of the coupler adapter 114 to ensure proper and secure installation of the coupler adapter 114 and the cap unit 112. By way of example, the alignment features 144 of the housing 116 in the present example comprise elongated axial recesses configured to receive axial protrusions 144 of the coupler adapter 114. The housing 116 further includes an outer-facing recess 148 sized and configured to receive the smart module 120 therein, and a cover 150 sized and configured to securely cover the recess 148 to form an enclosed chamber to protect the smart module 120 from damage. The cover 150 may include a pair of apertures 152 and surface markings 154 (e.g., FIGS. 23-26) as part of the user indicator functionality of the smart cap 110. The apertures 152 are configured to enable passage of at least a portion of a light pipe 156 therethrough, to uniformly transmit light from the first and second visual indicators (e.g., LED lights) 128, 130 mounted on the PCBA 126 to the user interface (e.g., exterior surface of the cover 150).

By way of example, the slider 118 is generally cylindrical in shape and has an exterior surface 158 and an inner lumen 160 extending therethrough. The inner lumen 160 is configured to snugly receive the medicine dispensing device 20 therein. By way of example, the slider 118 may have several portions having different diameters (of both the exterior surface 158 and the inner lumen 160) to snugly receive each part of the medicine dispensing device 20. For example, a first (e.g., proximal most) portion 162 may have the largest diameter and is configured to receive all parts of the medicine dispensing device 20 therethrough. A second (e.g., middle) portion 164 is configured to receive the needle cap and needle hub 26 therethrough, and snugly engage (e.g., by way of a friction fit) with the needle hub 26 (which is of uniform size among all injection devices), thereby coupling the slider 118 with the medicine dispensing device 20. A third (e.g., distal-most) portion 166 has the smallest relative diameter and is configured to allow passage of the needle and/or needle cap therethrough.

The slider 118 is configured to reside within the interior cavity 136 of the housing 116, and axially translate within the cavity 136 when a medicine dispensing device 20 is inserted into or removed from the smart cap 110 and interact with the deflectable detection switch 122 that extends into the cavity 136 through the switch aperture 137 from the underside of the PCBA 126. For example, the detection switch 122 may be biased in an "open" orientation, in which the detection switch 122 extends into the cavity 136. Likewise, the slider 118 may be proximally biased by way of spring 138 positioned between the distal portion of the slider and distal end of the cavity 136 such that the slider 118 does not contact the detection switch 122 when the smart cap 110 is not coupled with a medicine dispensing device 20. Upon insertion of a medicine dispensing device 20 into the inner cavity 136 of the housing 116, the medicine dispensing device 20 engages the slider 118 and pushes the slider 118 to translate distally, at which point a portion of the slider (e.g., the exterior surface 158 of the first portion 162) contacts the detection switch 122 and deflects the detection switch 122 into a "closed" position wherein the detection switch 122 contacts a trace element on the PCBA 126, thereby alerting the system that a medicine dispensing device 20 is coupled to the smart cap 110. To protect the electrical components comprising the smart module 120 housed within the outer-facing recess 148 from electrostatic discharge (ESD) and/or liquid (e.g., insulin from a broken cartridge or weeping out the end of the needle) that may otherwise enter the recess 148 through the switch aperture 137, the area around the switch 122 and switch aperture 137 may be waterproofed, for example by using one or more of a gasket, O-ring, hydrophobic materials (e.g., grease), or other similar waterproofing methods to fully isolate the electronics. By way of example, the base of the switch 122 and the PCBA 126 may have a water resistant conformal coating, and the switch 122 may be treated with a hydrophobic material (e.g., grease).

The coupler adapter 114 is provided to ensure that the smart cap 110 of the present disclosure may be securely engaged to and therefore used with the various third-party medicine dispensing devices 20 that may have different geometries. By way of example, the coupler adapter 114 is generally cylindrical in shape and has an axial lumen 168 extending therethrough, an alignment feature 170, a device engagement feature 172, and a locking mechanism 174. The axial lumen 168 is configured to receive a medicine dispensing device 20 therein. The alignment feature 170 is configured to interact with the alignment feature 144 of the housing 116 described above. By way of example, the alignment feature 170 of the present example comprises a pair of elongated axial protrusions configured to be slideably received with the elongated recesses 144 of the housing 116. The device engagement feature 172 may be any engagement feature configured to engage a complementary engagement feature on a medicine dispensing device 20, and may vary depending upon the user's particular device. By way of example, the device engagement 172 of the coupler adapter 114 described herein comprises a circumferential recess (e.g., complete or interrupted) configured to receive a beveled post 28 (or similar feature) of the medical dispensing device 20 to create a reversible snap-fit engagement between the medical dispensing device 20 and the coupler adapter 114. The locking mechanism 174 may be any mechanism suitable to securely couple the coupler adapter 114 to the housing 116, including but not limited to the cantilever locking element 174 (by way of example) configured to engage the aperture or recess 146 of the housing 116.

The coupler adapter 114 may be provided in various sizes and with various dispensing device coupling mechanisms to couple with different dispensing devices 20. In some implementations, the smart cap 110 may be provided as a kit with several different coupler adapters 114 to ensure the user is able to couple the smart cap 110 to their particular medicine dispensing device.

By way of example, as will be explained in further detail below, the first and second visual indicators 128, 130 provide a user output to inform the user whether it is safe to dose. As such, the first and second visual indicators 128, 130 may be color coded to give positive indication to the user whether or not to dose. For example, the first visual indicator 128 may be green to indicate that the user is OK to dose, and the second visual indicator 130 may be red to indicate that it is not safe to dose. Moreover, the cover 150 may be provided with surface markings 154 in the form of words (e.g., "YES" or "NO") and/or symbols (e.g., "+", "−", circle with a line through it, an arrow, stop sign, check mark, and the like) positioned next to each visual indicator 128, 130, to reinforce the light color.

Figure 11:
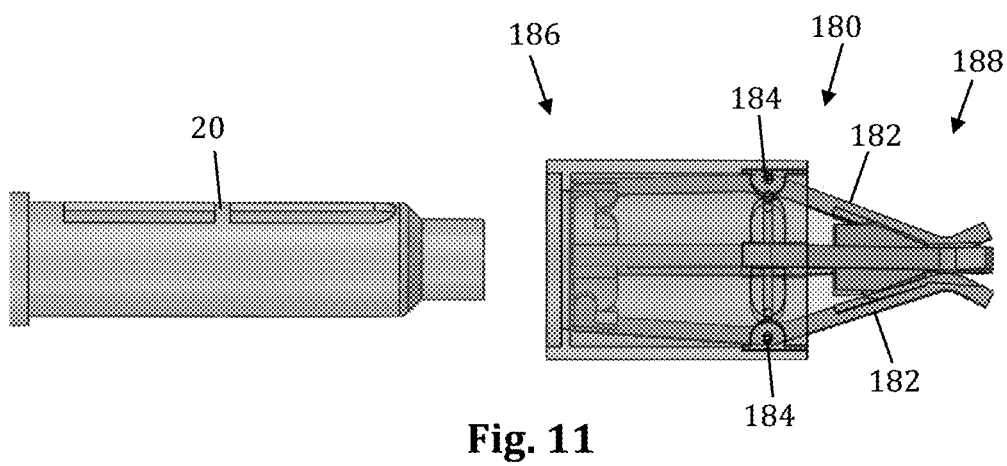
FIGS. 11-14 illustrate example embodiments for a smart cap including an example universal fit mechanism according to one aspect of the disclosure.
Figure 12:
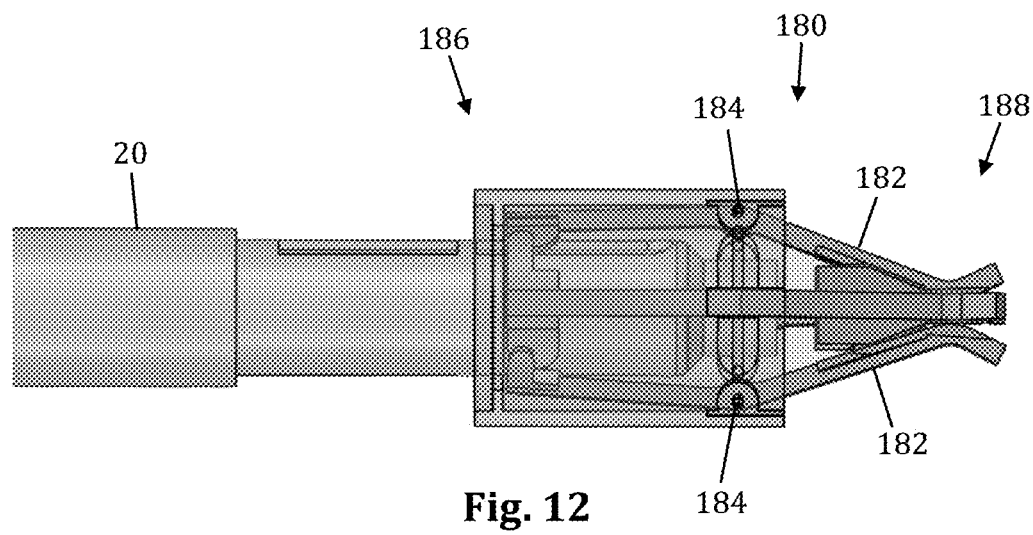
Figure 13:
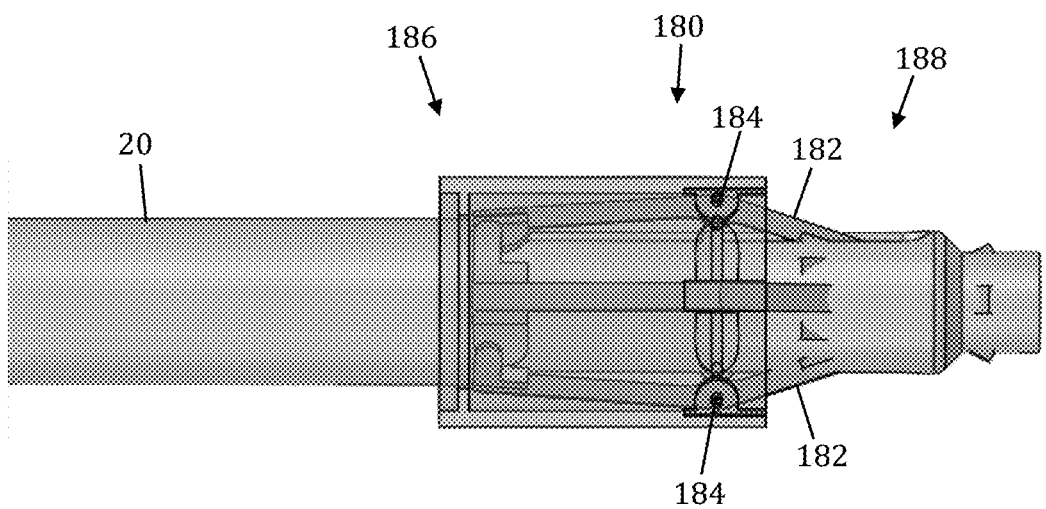
Figure 14:
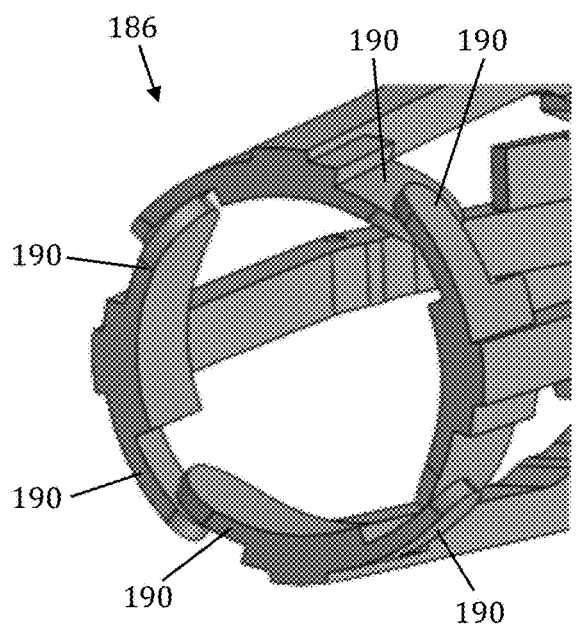

FIGS. 11-14 illustrate an example of a universal fit mechanism 180 that the smart cap 110 of the present disclosure may employ to enable the smart cap 110 to engage with any available medicine dispensing device or injector 20. By way of example, the universal fit mechanism 180 may comprise spring-loaded or elastically deformable arms 182 that expand as needed to allow different sized injectors 20 to fit. The arms 182 may have a middle hinge mechanism 184 such that (as shown in FIG. 11) the proximal ends 186 of the arms 182 are fully expanded for installation of the tip of the injector 20 (especially important if a sterile needle is installed) and (as shown in FIG. 12) only lightly contact the injector 20 during most of the installation motion. When the injector 20 is nearly fully installed, the end the distal end of the injector contacts the distal ends 188 of the arms 182, expanding them radially outward and pivoting about the hinge point, which applies an inward radial force at the proximal end 186 of the arms 182, causing the arms 182 to securely engage the injector 20. As shown in FIG. 14, overlapping flanges 189 on the proximal end 186 create an aperture that closes in diameter to engage the injector 20 as the arms 182 pivot about the hinge mechanism 184.

FIGS. 15-21 illustrate an example of a smart tracking accessory in the form of a smart cap 210 configured to interact with a medicine dispensing device 20 according to one embodiment of the disclosure.

Figure 15:
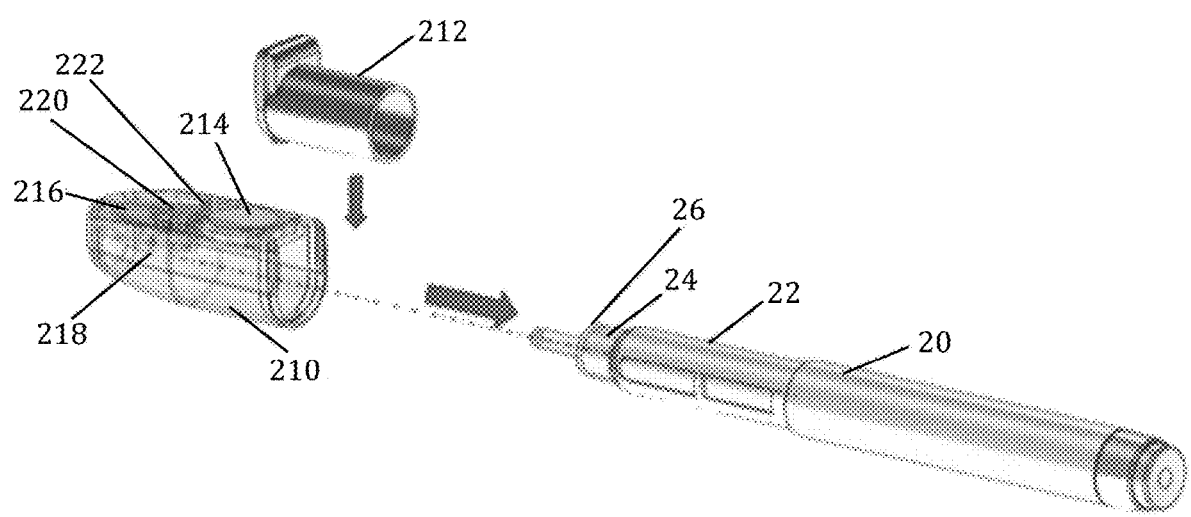
FIG. 15 is a partially exploded perspective view of another example of an intelligent tracking accessory coupled with a medicine dispensing device, forming part of the intelligent medicine administering system of FIG. 1.

By way of example, FIG. 15 shows a diagram of a smart cap 210 with an installable coupler adapter 212, which may be used as a cap for injector 20. The smart cap 210 includes battery 214, electronics PCB 216, switch contact arm 218, first visual indicator (e.g., green LED) 220 and second visual indicator (e.g., red LED) 222. In some embodiments, the visual indicators 220, 222 are mounted to the electronics PCB 216 and are visible outside the device either through cutout windows, a lens, light pipes, or through a translucent outer casing of the smart cap 210. In some implementations, for example, the user slides coupler adapter 212 to mate with the smart cap 210, snapping non-permanently into place so that it is attached as a single cap unit for the user, but may be removed and replaced with a different coupler adapter (not shown) that is sized to fit with a different dispensing device. Multiple coupler adapters may be included with the product so that the user may install the appropriate one for their dispensing device 20. Alternately, in some examples, the coupler adapter may be permanently factory-installed so that the device is permanently configured for a single type of dispensing device.

For example, since the coupler adapter 212 is installed and detached perpendicularly to the direction of installation onto the dispensing device or injector pen 20, it forms a shape lock when installed onto the injector pen 20 preventing accidental detaching of the coupler adapter 212. Additionally, since the coupler adapter 212 is installed from the side of the switch contact arm 218, this ensures that even if the coupler adapter 212 is not fully seated or comes partially unsnapped, this only increases engagement of the switch contact arm 218 with the threaded needle interface 24 or needle hub 26, ensuring robust actuation of the switch 226.

Figure 16:
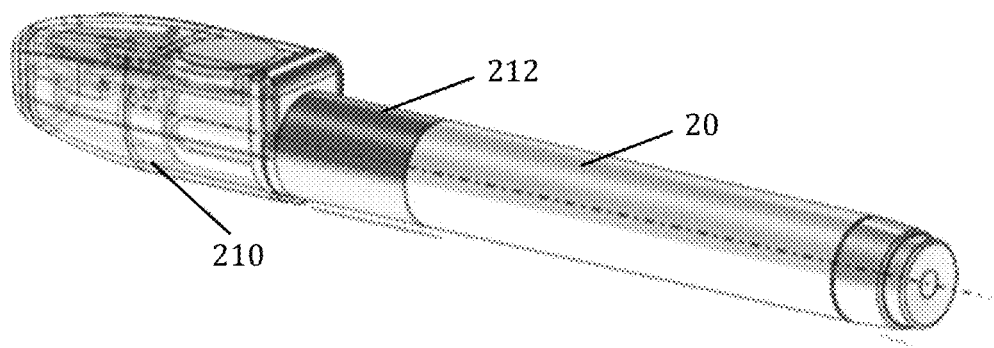
FIG. 16 is a perspective view of the intelligent tracking accessory and medicine dispensing device combination of FIG. 15.

When the cap assembly, including smart cap 210 with coupler adapter 212 attached, is installed onto the injector pen 20 by the user, as shown in FIG. 16, the switch contact arm 218 contacts the threaded needle interface 24, or if installed, the needle hub 26.

FIGS. 17-21 show cut-away diagrams depicting an example switching mechanism in a smart cap 210 in accordance with the present technology.

Figure 17:
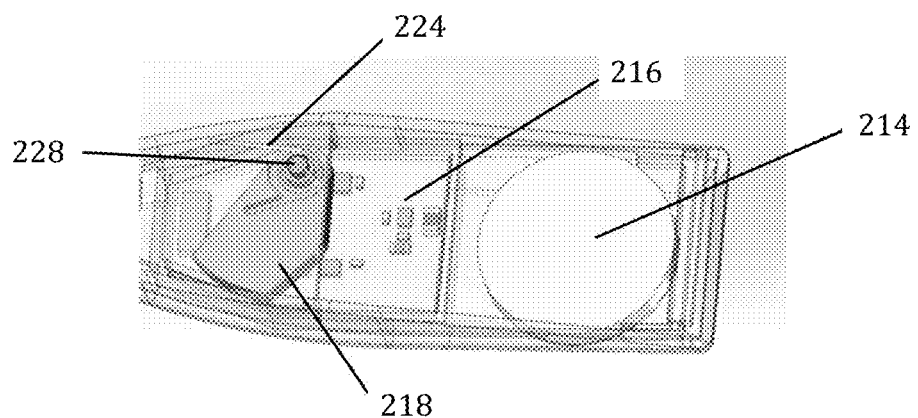
Figure 18:
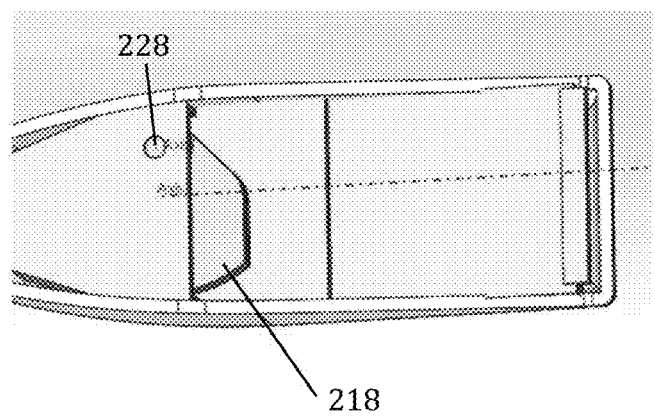

By way of example, FIG. 17 shows a cut-away view of the underside of the example smart module 210 with the switch contact arm 218 pivoted forward as when an injector pen 20 is installed. Switch return spring 224 is configured to bias the switch contact arm 218 pivoted back in the opposite direction when an injector pen 20 is not installed. FIG. 18 shows a cut-away view of the underside of the smart module 210, showing the switch contact arm 218 pivoted back, as when an injector pen 20 is not installed. FIG. 19 shows a cut-away view of the switch contact arm 218 in its rest position, with an injector pen 20 installed showing that contact is made, and the switch contact arm 218 would be pivoted forward.

FIG. 20 shows a cut-away view of the top of the switch contact arm 218 and its engagement with electrical switch 226, which is mounted on the electronics PCB (hidden in this view). Switch contact arm 218 pivots about switch contact arm post 228 which contains switch contact arm post protrusion 230. The protrusion is oriented such that it engages electrical switch 226 when the arm is pivoted forward (e.g., with injector pen 20 installed) and does not engage electrical switch 226 when it is pivoted back (e.g., with injector pen 20 not installed). Alternatively, in some examples, it may be configured to actuate the switch only when the injector pen 20 is not installed, and not actuate the switch when the injector pen is installed.

The use of a switch contact arm 218 allows the electrical components to be contained within the enclosure, better isolated from electrostatic discharge (ESD) and liquid (e.g., insulin from a broken cartridge or weeping out the end of the needle) than if it were exposed to directly contact portions of the injector pen and/or needle. The switch contact arm post 218 may be fully sealed with a gasket, O-ring, hydrophobic materials (e.g., grease), or other similar waterproofing methods to fully isolate the electronics.

One key feature of the smart cap 110 is the detection of user interaction with the medicine dispensing device 20, including sensing when the smart cap 110 is removed from and/or coupled to the medicine dispensing device 20. This detection may be accomplished by way of a physical contact switch that is actuated by presence of the medicine dispensing device 20, for example as described above with respect to smart cap 110 and smart cap 210. A module that is designed to work with multiple different dispensers 20 may contact the needle hub portion 26 of the dispensing device 20, as this is standardized and therefore guaranteed to be similar across all dispensers. Geometry of the needle hub 26 is similar to (e.g., only slightly larger than) the threads 24 that are exposed when a needle is removed, so preferably the switch will activate on the needle threads 24 or the needle hub 26 itself, so that the detection is accurate whether or not the user left a needle installed. In some implementations, the smart cap 110 may detect the medicine dispensing device 20 by sensing the presence of the device 20 or the drug it contains via capacitive sensing. This may be done through the plastic of a cap, enabling sealed devices or clip-on sensors that fit outside of a dispenser's original plastic cap. In some implementations, the medicine dispensing device 20 may be detected optically with a photo emitter and photo detector, which may detect a beam of light broken by the dispenser, indicating the presence or absence of it within the cap.

As an additional safety mitigation for potential lack of communication between the user's smart tracking accessory (such as the example smart cap embodiments 110, 210 described herein) and the user's companion device 30 (e.g., smartphone, tablet, wearable communication device, etc.), the smart tracking accessory itself may comprise limited output to inform the user of critical information even if wireless communications have not occurred.

A limitation of this output is battery power, especially when a permanent battery is used that must last the lifetime of the device regardless of the user's behavior.

One example of direct user output is one or more visual indicators, for example LED lights 128, 130 of the smart cap 110 and/or LED lights 220, 222 of the smart cap 210. It is noted that LED lights are just one embodiment of visual indicators described herein by way of example, and other embodiments of visual indicators may be used with or instead of LED lights as described herein, such as any electronically actuated visual indicator including but not limited to a light, e-ink display, OLED, and liquid crystal display/LCD output, among others. In some implementations, the health management app 40 installed on the user's companion device 30 may be used to set up dose scheduling settings, transmit these settings to the smart accessory, and then the smart accessory would illuminate visual indicators appropriately based on these settings.

In one embodiment, the smart tracking accessory may comprise a single visual indicator (e.g., LED) which is illuminated when the smart accessory determines that it is time to take a dose (e.g., using the real-time clock module 132 in combination with a recorded time of last dose or normal dosing schedule to calculate the dose interval), or when it is safe to take a dose (e.g., some threshold before the scheduled dose time). This light may be lit constantly, or to reduce power consumption, may flash at an interval. Alternatively a light may illuminate when a dose has been taken and the user should not dose, however, illumination when it is time to dose is preferred because this is failsafe—in case of a depleted battery or software error the LED will not illuminate.

In some embodiments, for example the smart caps 110, 210 described herein, the smart accessory may include two visual indicators (e.g., LED lights), including a first (e.g., green) LED light 128, 220 indicating that it is time to dose (e.g., safe to dose or within a safe dosing time window), and a second (e.g., red) LED light 130, 222 indicating that a dose has been taken and the user should not dose again (e.g., unsafe to dose). A bi-color visual indicator could serve the same function, but two separate LEDs are preferred so that a colorblind user can still differentiate them. Additionally, the surface of the smart accessory near the LED lights (e.g., cover 150) may include surface markings (e.g., words and/or symbols) corresponding to the light color to reinforce the message of the particular light. In some embodiments, the LED lights may illuminate constantly, though this requires substantial power. In some embodiments, the LED lights may flash intermittently, which is an improvement, but still requires significant power, most of which goes to waste when the user is not in the vicinity of the pen and does not need the alert flashing.

Figure 22:
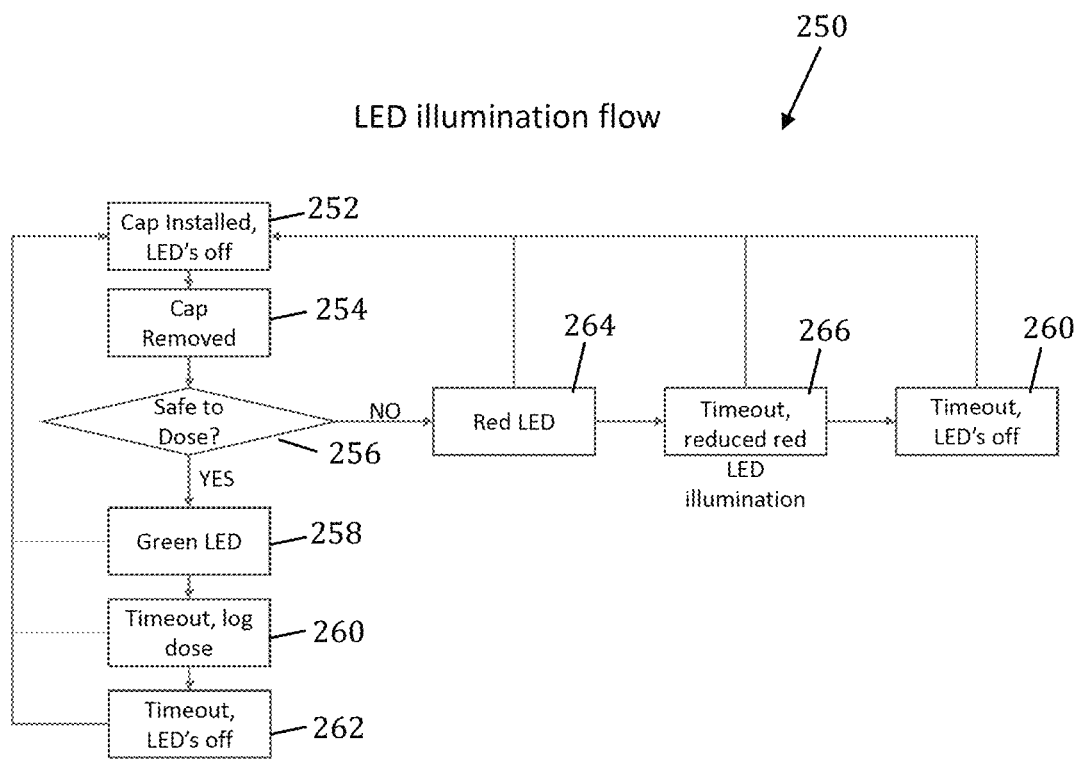
FIG. 22 is a flowchart depicting an example LED illumination flow for the intelligent tracking accessory of FIG. 3.
Figure 23:
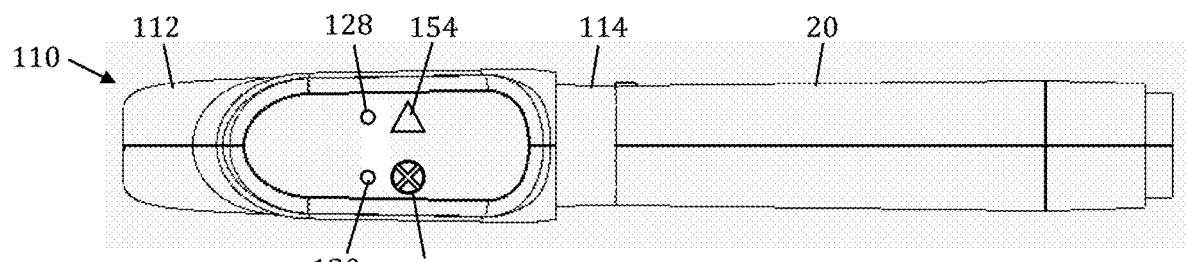
FIGS. 23-26 are plan views of the intelligent tracking accessory and medicine injection device combination of FIG. 5, illustrating in particular various LED illumination scenarios.
Figure 24:
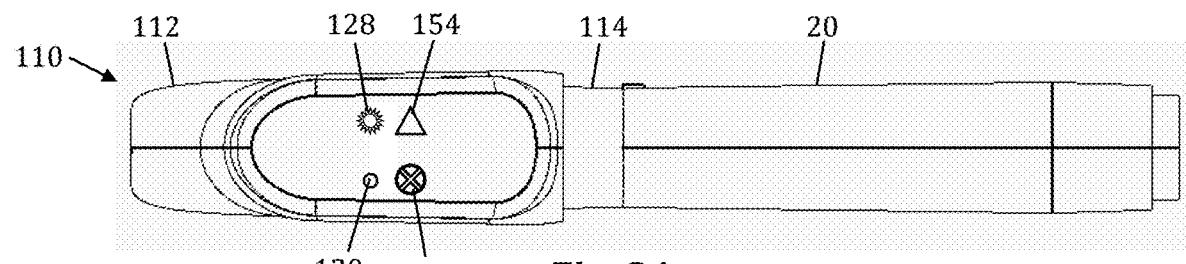

As illustrated in FIGS. 22-26, in some implementations of the tracking accessory with two LED lights (e.g., smart cap 110 described herein), neither the first LED light 128 nor the second LED light 130 is illuminated until the user interacts with the medicine injection device 20 (e.g., removes the smart cap 110), at which point the appropriate LED light illuminates. FIG. 22 illustrates an example of an example LED illumination flow 250 according to one embodiment. By way of example, when the smart cap 110 is initially coupled (e.g., box 252) to the medicine injection device 20, the detection switch 122 is deflected such that it is in contact with trace elements on the PCBA 126 and the smart cap 110 detects the presence of the injection device 20. At this point both the first and second LED lights 128, 130 are off, for example as shown in FIG. 23. When a cap removal event (e.g., box 254) occurs, the detection switch 122 is released from contact with the trace elements on the PCBA 126, triggering the smart cap 110 to determine whether it is safe for the user to dose (e.g., box 256). If the answer is "Yes" (e.g., the scheduled dose event or the time since last dosing event is in a valid window) then the smart cap 110 will cause illumination of the first or green LED light 128 (e.g., box 258) as shown by way of example in FIG. 122. By way of example, the green LED light 128 may remain illuminated while the smart cap 110 performs a timeout to allow for a predetermined period of time sufficient for the user to administer a dose of medicine from the injection device 20, as measured from the time (indicated by the real-time clock 132 and recorded by the processor 131) elapsed since the cap removal event occurred. Once this predetermined period has elapsed, the smart cap 110 will log a successful dose event (e.g., box 260) and either communicate this dose event (e.g., via the communications module 134) to the user's nearby companion device 30 or store the dose event in the data storage module 133 for later communication to the user's companion device 30, for example if the user's companion device is not in wireless communication range of the smart cap 110 at the time of the dose event. If the user replaces the smart cap 110 before the expiration of a predetermined amount of time sufficient to administer a dose, then the smart cap 110 will not log a therapeutic dose event, and optionally may log the occurrence of a status check event. After the smart cap 110 performs another timeout (e.g., box 262), for example to ensure that a dose was delivered (e.g., via positive confirmation from the user and/or user's companion device, or another indicator) then the smart cap 110 will cause the LED light 128 to turn off and return to the initial state of both lights being off.

Figure 25:
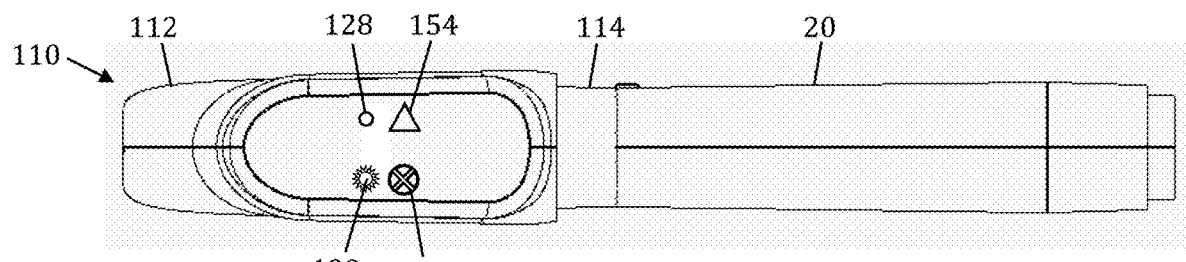

If the smart cap 110 determines that it is not safe to dose at box 256 (e.g., the time clock 132 indicates a time that is not within the scheduled or safe dosing window), then the smart cap 110 will cause illumination of the second or red LED light 130 (e.g., box 264), as shown by way of example in FIG. 25. After a certain amount of time has passed (e.g., box 266), the red LED light 130 may remain on but at a reduced illumination to conserve power (see below). After another predetermined period of time, the smart cap 110 will cause the LED light 130 to turn off and return to the initial state of both lights being off (e.g., box 268). It should be noted that, upon determining that the user interaction event occurred in an unsafe-to-dose period, the smart cap 110 will not log a dose event no matter how much time elapses until the smart cap 110 is replaced on the injection device 20.

The time outs referenced above may occur for several reasons. For example, the red or green LED lights 128, 130 may illuminate for several seconds after user interaction to give time for the user to acknowledge the red or green indication. A red indication (e.g., indicating not safe to dose) may persist while the cap is removed, but a green indication (e.g., indicating safe to dose) should not persist for a significant amount of time, e.g., longer than approximately one minute. In this time, it is possible the user may have taken a dose, so it would be unsafe to continue indicating that it is safe to dose, in case the user doses, is distracted, and then perceives an indication to dose again.

In addition to timing-out for safety, the LED lights 128, 130 may time out for power savings. For example, a red LED light 130 may illuminate brightly or at high duty cycle for several seconds, and then transition to a lower-power illumination with less brightness and/or lower duty-cycle to give the clearest indication to the user immediately, and then conserve power afterward when the user is not likely to be looking at the LED lights.

To further reduce power consumption of LED lights, the LED lights 128, 130 may blink rather than be steadily illuminated. For example, the LED lights may illuminate for 100 milliseconds every 1 second. In some implementations, the green and red LED lights 128, 130 may blink at different rates for improved visual differentiation. In some examples, the red LED light 130 would flash at a faster rate (e.g., 2× per second) than the green LED light 128 (e.g., 1× per second) to be more attention-getting in the safety critical situation, alerting the user not to dose.

Figure 26:
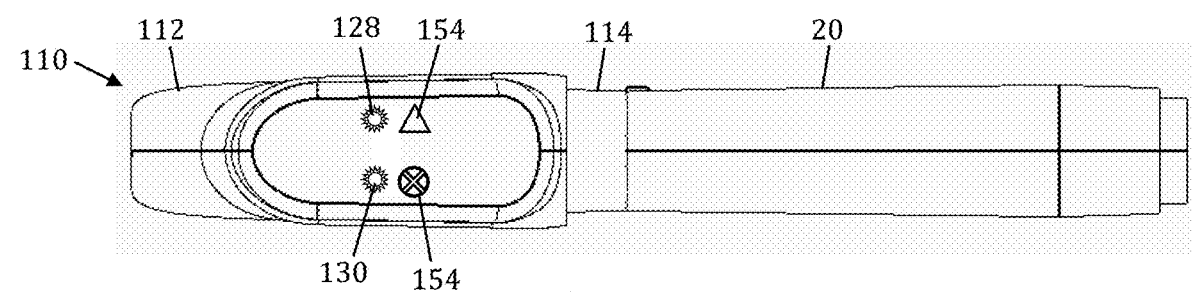

In some implementations of the smart accessory with two LED lights, the device may also illuminate both LED lights 128, 130 as shown by way of example in FIG. 26, e.g., together or in alternating flashes, to indicate that the user should check their companion device 30 for a message. By way of example, the message may include (but is not limited to) a low battery alert, a high or low temperature alert indicating that the insulin may be degraded, or a message to change to a new dose size based on a therapy change or titration adjustment.

As alternatives to the LED behavior described above, an LED on the example smart accessory may begin blinking when it is time to take a dose, even if the user has not yet interacted with the device. This may serve as a reminder, noticeable from a distance. Additionally, if equipped with a screen, the smart accessory may output dosing information directly, such as the time of the last dose, time of the next dose, battery state, communication status with the user's companion device 30, and dose size to take.

In some embodiments, the smart cap 110 may have only a single input switch (activated when the injector is installed or removed) and limited output (such as an LED) or no output at all. This presents a challenge for securely pairing wirelessly to a companion device 30. For example, in the case of Bluetooth pairing an example smart cap 110 to a companion device 30, the smart cap 110 may have a hard-coded security key listed in the product labeling, it may have a graphical or QR code that can be scanned by the companion device 30 camera which contains the security key.

In some embodiments, if the smart cap 110 is equipped with LEDs or other visual output, these could be programmed to flash at a specific interval or pattern that could be identified by the companion device 30 camera. This pattern could either contain a digitally encoded security key, or the precise timing could be used to confirm that the companion device 30 and smart cap 110 are in close proximity.

To verify that a health management app 40 user has the smart cap 110 in their possession, the accessory may illuminate (or flash/blink to save power) one or more LEDs and request the user to indicate which LEDs (e.g., red, green, or both red and green) are illuminated. This may be performed multiple times in sequence to form a security key that only a user with the actual smart cap 110 would know, and a hacker or another user attempting to pair to a different accessory would not know. To avoid confusion, the sequence may be configured to not display the same state (e.g., red, green or both) twice in a row, and similarly the sequence may avoid using the "off" state (e.g., no lights illuminated). Also, in some embodiments the sequence may (due to omitting the off state and/or omitting the previous state) be limited to 2 or 3 possible states per step in the sequence. The security key may be encoded as pulse timing (e.g., asking the user to tap a button displayed by the app 40 on the user interface of the companion device 30 immediately upon LED illumination, so that timing information can be compared), as color (e.g., asking the user to indicate which color or colors are illuminated), or as a blink sequence (e.g., asking the user to indicate how many times the light flashes). Once this information is accumulated in the app 40, it may be used to verify authenticity when pairing to the smart cap 110.

As a further protection against unintended pairing, the system may request that the user install and remove the smart cap 110 multiple times with specific timing and/or in a specific sequence, and upon detecting this timing and/or sequence the smart cap 110 may enable pairing to a new device. By prescribing multiple installations and removals within a brief time period, the system ensures that the smart cap 110 cannot be accidentally paired to a new device from normal use, which would typically only involve a single installation and removal within a brief time period. The app 40 could further prescribe time delays between user actions, which could be used to further reduce the chances of accidentally triggering the sequence, and could be used to confirm authenticity. For example, if the app 40 requests that the user install the smart cap 110, then pauses for 5 seconds before requesting that the user remove the cap 110 again, the app 40 may disregard multiple installations and removals that are spaced less than 5 seconds apart. Or if the pause time is a random variable, and multiple installations and removals are performed in sequence, the cap 110 may detect the time delays between user interactions and use these as a unique code (for example, delays of 5 seconds, 2 seconds, and 8 seconds could form the unique code "528"). This unique code may be used to verify authenticity when pairing as well.

In a similar fashion, if the app 40 requests that the user perform an action (e.g., remove the smart cap 110) and confirm when it has been done, the app 40 has a defined time window in which this action would have occurred. By defining multiple time windows, again, a unique code may be generated and used to confirm authenticity between the accessory (e.g., smart cap 110) and companion device 30.

One challenge of tracking usage of a medicine injection device 20 with a health management software app 40 on a companion device 30 is that the injection device 20 may not be within range of the companion device 30. This is especially true for devices 20 that may only be used once a day on a regular schedule (e.g., long-acting insulin pens) since they are often left in a personal location (e.g., bathroom, nightstand, refrigerator) that the user may rarely bring their companion device 30 to.

In cases where the smart accessory such as the smart cap 110 must communicate directly with a companion device 30 that is only occasionally in range, and the accessory is battery-operated and must conserve power, strength and time intervals of communication attempts can be optimized based on risk and usefulness. For example, the most critical times to establish wireless communication between the smart cap 110 and the companion device 30 and ensure the user has up-to-date information are right before a dose is to be taken (e.g., to verify that it has not already been taken), and for a time after a dose has been taken until it is confirmed to have been received (e.g., to ensure the user does not double-dose); so these would be the periods with the most frequent communication attempts, drawing the greatest power usage. After a dose, once the accessory 110 confirms receipt by the companion device 30, it may discontinue communication attempts as there is no longer new data to transfer. However, if the smart accessory 110 does not establish wireless communication with the companion device 30 for an extended period of time, the smart accessory 110 may reduce communication attempts to save power as the data becomes less critical. As such, the disclosed smart accessory (e.g., smart cap 110) may implement staged communication attempts that are more 'aggressive' when they are most critical. Once a typical dosing time window has passed (e.g., 2 hours past the scheduled dose time), the chance of the user double-dosing is reduced, and so power may be conserved by attempting communications less frequently. Once the action time of the drug has substantially passed and/or once it is no longer unsafe to dose again, communication attempts may be further reduced or discontinued as there is no longer a risk of double-dose. In such implementations, the smart accessory such as the smart cap 110 is spending RF power only when it's useful to the patient, based on the action time of the drug (e.g., only when it would be dangerous to dose again).

Figure 27:
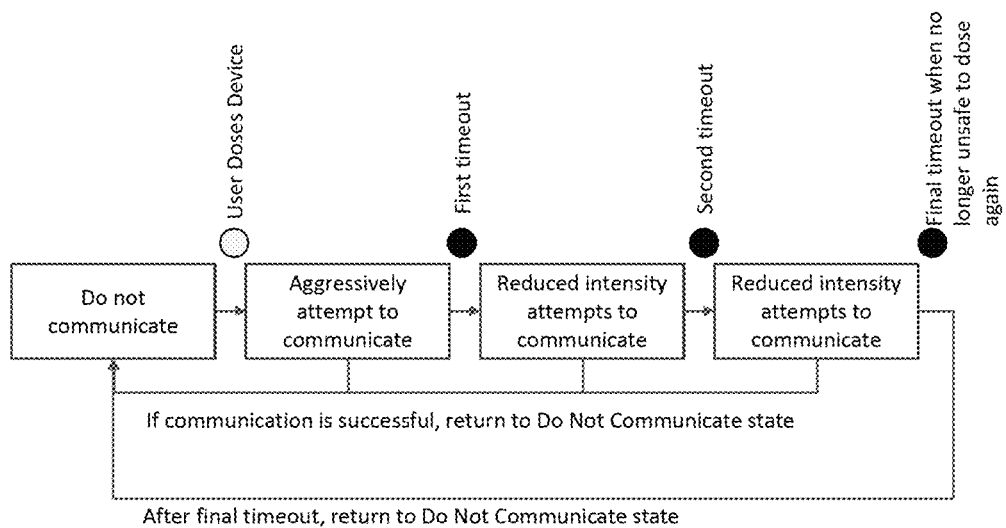
FIG. 27 is a flowchart depicting an example wireless communications method for communicating new doses from an intelligent tracking accessory to a companion device forming part of the intelligent medicine administering system of FIG. 1.
Figure 28:
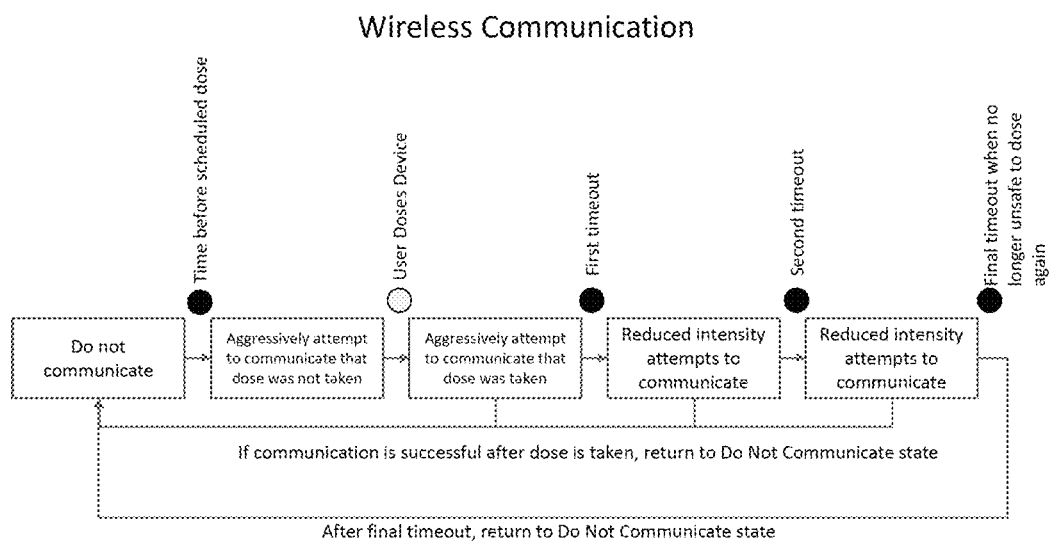
FIG. 28 is a flowchart depicting an example wireless communications method for confirming a dose is not yet taken and communicating new doses.
Figure 29:
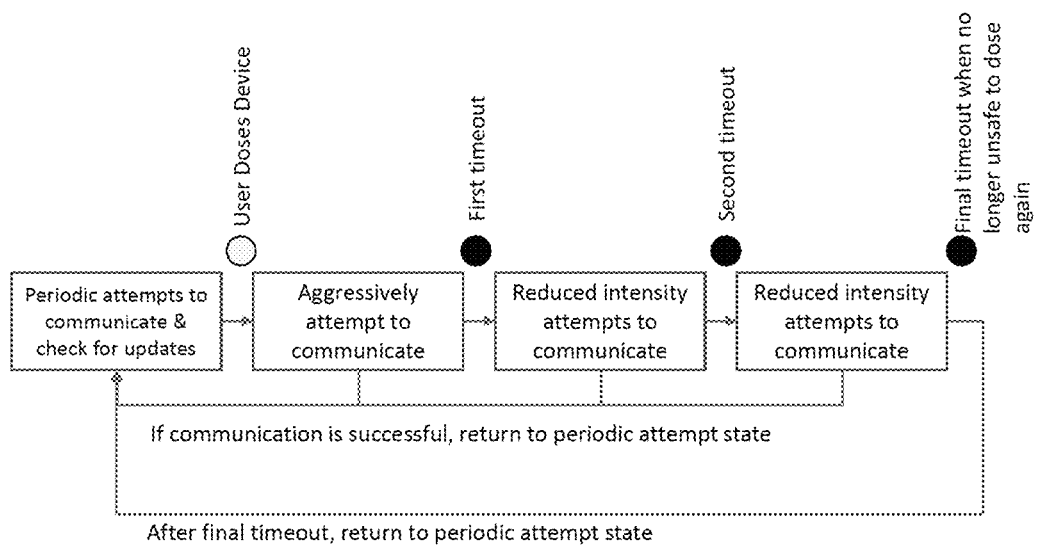
FIG. 29 is a flowchart depicting an example wireless communications method for communicating new doses and checking for updates periodically.

FIGS. 27-29 show diagrams of example wireless communications methods between a smart accessory (e.g., smart cap 110) and a companion device 30. FIG. 27 shows a method for communicating data relative to new doses to the companion device 30. FIG. 28 shows a method for confirming with the companion device 30 that a dose is not yet taken and also communicating data relative to new doses to the companion device 30. FIG. 29 shows a method for communicating data relative to new doses to the companion device 30 and checking the companion device 30 for updates periodically.

In addition to communicating dose information from the smart accessory to the companion device 30, the companion device 30 may need to communicate settings or database changes to the smart accessory 110. For this reason, even when there is not a dose to communicate, the smart accessory 110 may continue to communicate periodically with the companion device 30 to check for updates. These changes are less critical for safety so some time lag is acceptable. For this reason, when there is no dose to communicate, the smart accessory may infrequently (for example, every 5 minutes) attempt to connect with the companion device 30, allowing it to get any updates with a minimal amount of power expended.

A more aggressive approach would transmit very frequently (for example, every 10 seconds) for a time period leading up to a dose reminder to positively confirm with the companion device 30 that the dose had not yet been taken. For example, the smart cap 110 is configured with a variable reflecting when the user should be dosing, and a variable reflecting when the companion device 30 will remind them to dose, so it can intelligently begin beaconing around this time. By establishing this robust communication, the companion device 30 may then affirmatively assure the user that the dose had not been taken if the accessory is within range, or may affirmatively warn the user that the smart accessory is out of range and dosing information is not up to date. This would prevent the companion device 30 from instructing the user to dose when they had already dosed but simply had the device out of communication range of the companion device 30.

To conserve power over the lifetime of a smart tracking device (e.g., smart cap 110) that has a permanent (e.g., non-replaceable and non-rechargeable) battery 124, past communication success may trigger alternate communication schemes that balance power usage differently between attempting to communicate immediately after a dose versus attempting to communicate for many hours following. For example, a user whose companion device 30 is rarely within range of the smart accessory 110 immediately after a dose does not benefit from aggressive (e.g., high power usage) communication attempts immediately after a dose.

In some implementations, the smart accessory may respond to one or more of the following triggers: percent of successful communications within a time threshold of a dose being taken, average or median connection time after a dose is taken, and/or remaining battery voltage or estimated capacity. When one of these triggering thresholds is met, the smart accessory may reduce the aggressiveness (e.g., strength and/or frequency) of communication attempts for the time period immediately after a dose, conserving more power for the many hours of communication attempts that may occur.

In some implementations, another option to ensure communications even if the user's companion device 30 is out of range is for the tracking accessory to communicate via Wi-Fi, cellular data, or other wireless means to the internet, allowing the smart tracking accessory and the user's companion device 30 to store data and retrieve updates from a central server 50 (e.g., "the cloud") instead of being in direct communication.

In some instances, a user may interact with their injection device 20 in a way that activates the smart accessory 110 but does not administer a dose. For example, they may remove the smart cap 110 of an insulin pen to check the insulin quality or amount remaining. Or they may remove the smart cap 110 to trigger the indicator LEDs to see if a dose is needed. They may see that a dose is not needed, or the user may see that a dose is needed but want to take the dose at another time—in either case, the user would replace the smart cap 110 without taking a dose. If the cap 110 immediately logs a dose, this presents a problem of non-doses or null events being logged in the user's database. Also, in cases in which the user chooses to delay administering a dose when the smart cap 110 indicates that a dose should be taken (e.g., the green LED light 128 is illuminated), after replacing the cap 110 and removing the cap a second time, the smart cap 110 would indicate that the dose had already been taken and alert the user not to dose the next time they interact with the device (e.g., by illuminating the red LED light 130 upon second cap removal event), potentially leading them to miss a dose.

As a mitigation, the smart tracking device 110 may be programmed to include a brief time period after a cap removal event occurs that the cap may be replaced to avoid logging a null event as a dose. Implementing this mitigation technique can enable the dose tracking system to operate without logging null events and giving incorrect readings.

For example, administering a dose requires several seconds to install a needle or remove a needle cover, prime the pen, dial the selected dose, inject the dose, and remove the needle or replace the needle cover. A preset minimum threshold, for example 5 seconds, may be set such that any cap removal for less than this duration may be identified as a null event and not be logged as a dose. Alternatively, for example, the device may adjust this threshold based on past user behavior. For example, if the average time the cap is removed for a dose is 30 seconds, the minimum threshold may be set to some percent of that, for example 50% or 15 seconds for that individual user.

As an alternate mitigation, in some implementations for example, the smart accessory may contain two detection switches that activate at different depths of installation onto a pen, or a single analog sensor (such as capacitive) that can detect varying depths of installation onto a pen. Unsnapping the cap and partially removing it would activate the visual indicator to the user but would not cause the accessory to log a dose. Only fully removing the cap (e.g., activating the second detection switch, or driving the analog sensor above a threshold) would initiate logging of a dose. In this way, a user may partially remove the cap for any amount of time to observe the visual indicators and then re-install the cap without taking a dose, and a false dose will not be logged.

As an alternate mitigation, for example, the smart accessory may contain an orientation sensor to track movement of the smart cap 110. The use of an Inertial Measurement Unit (IMU) can digitize the rotation and translation of the cap 110 after it is removed from the pen 20. The pattern of use can then be analyzed to infer how the cap was handled. Detected acceleration and/or rotation above a certain threshold would indicate that the cap 110 was taken fully off of the injection device 20 and set down while a dose was taken, whereas below the threshold would indicate that a dose was not taken.

In special cases, the smart accessory may communicate with the companion device 30 to request user confirmation of whether a dose was truly taken or not. This may occur when the cap 110 is removed for a time very near the minimum threshold and it is uncertain whether a dose was taken. It may also occur when a dose was not recommended but the cap was removed for an extended time, implying a double-dose. If the double-dose was not taken, the database in the app 40 may be corrected to remove the duplicate entry. If the double-dose was taken, the user may need to take emergency actions or seek assistance, so the app 40 may prompt them to do so and/or alert emergency contacts automatically. The app 40 may automatically alert emergency contacts if the user fails to manually indicate that the double-dose was not taken to provide additional safety in case the user does not see the notification or is not able to respond appropriately due to overdose.

If the cap 110 is removed for an extended period of time, indicating that the user may have forgotten to replace it on the pen 20, the app 40 may additionally remind the user to replace the cap 110.

In cases where the cap logs a dose and syncs it to the user's companion device 30, the user may manually edit their logbook and indicate that a dose was not actually taken. In this case, the companion device 30 would communicate this information to the cap 110 so that it may indicate "green" or "ok to dose" the next time the user removes the cap 110.

In some implementations, the smart accessory communicates dosing information to an app 40 resident on the user's injection device 20, companion device 30, or both, to be logged in a database of the system 10. The app 40 communicates information to the accessory (e.g., smart cap 110) as well, such as dose scheduling (e.g., doses per day, time of day for each dose), recent doses (e.g., any manually entered or deleted doses, so that the accessory may prompt the user correctly to take or not take a dose), or alert states (e.g., changes to therapy or other fault conditions). Nominally the smart cap 110 and companion device 30 are always in sync and up to date, but there may be cases where the user's companion device 30 is out of range or powered off. In this condition, the accessory may continue to function standalone with the last synced settings and dose history.

Yet, in some embodiments, a smart accessory can include a smart cap 110 that functions as a fully standalone device if it is preprogrammed for dosing interval or has a selector switch to select, e.g., 1 dose per 12 hr, 24 hr, 48 hr, or the like. In this embodiment, for example, the smart cap 110 can initially indicate green, and would then indicate red until the dosing interval had passed, for example 12, 24, or 48 hours later. To accommodate slight variations in dosing times, the accessory may indicate green some time threshold before the next dose time. For example, it may indicate green 2 hours before the next dose. This would result in displaying red for 10, 22, or 46 hours after a dose was taken, depending on the schedule setting. This cap 110 could function as a simple reminder aid with no database, or could store dosing history for many weeks or months, allowing download by a physician or caregiver for evaluation even if the user does not use a connected health maintenance app 40.

In addition to dosing instructions (e.g., time for next dose, dose amount), for example, the disclosed system may calculate compliance metrics to display to the patient user or physician or caregiver. These may be displayed in a PDF report, in a real-time app display, or on a screen or other graphical output on the accessory device itself.

Compliance metrics may include but are not limited to:
1. Days since a dose was missed;
2. Days in a row of successful doses;
3. Doses in a row successfully taken without missing one;
4. Percent of doses correctly taken in the past week or month;
5. Cumulative doses taken since a counter was last reset (e.g., at the last physician's appointment); and/or
6. Days remaining until a goal of successful doses in a row is achieved (e.g., 90 days of no missed doses).

For battery-operated devices, especially with permanent non-rechargeable and non-replaceable batteries, lifetime power consumption must be minimized. This is especially important for the time the device is stored prior to use (e.g., in the original packaging, prior to the user receiving or beginning to use the device) as this shelf life period can be several years in duration.

In some embodiments, the smart accessory device may have a pull-tab that insulates power contacts, such that when the user removes the tab the device is powered-on. The tab may be manually removed, or may be attached to the packaging such that removal from packaging activates the device.

In some embodiments, the smart accessory device may have a contact switch that activates the first time an injection device 20 is installed into it. In the case of a cap unit 112 and separate coupler adapters 114, the adapter 114 may be configured to actuate a physical contact switch in the cap unit 112, or may itself have a conductive element to complete the power circuit in the module, powering on the device when an adapter is first installed.

In some implementations, the switch options may complete the power circuit to power the device directly, or may be configured to actuate a latching switch such that the device remains powered-on for the rest of its use life, regardless of the state of the switch or removal of adapters after initial power-up.

In some implementations, the main switch that detects attachment of the cap to the injector may also serve to power-on the device upon initial use. Once initially powered-on, the circuit can latch the power supply such that the device would not fully power off when the cap is then removed.

In typical use, for example, a smart cap 110 is installed onto a pen for the majority of its use life and is detached for a small portion of its use life. For this reason, it is desirable to configure the device with a switch that is closed (e.g., connected) when the cap is removed and open (e.g., disconnected) when the cap is installed. However, during storage prior to use there is no pen installed, leaving the switch in its higher-powered state if the device is not fully depowered, diminishing shelf-life. To mitigate this, the device may be shipped with a component or feature of the packaging that holds the switch open (e.g., as if an injector were installed) to maintain the low-power state prior to use.

A large switch mechanism configured to detect the installation of an injector may have sufficient mass that it is subject to false triggering from drop or vibration in transit. If, as described, this switch also permanently powers-up the device, this would cause premature battery drain while in storage. One mitigation is the component or feature of packaging described that holds the switch in the open position so that it cannot freely move even if subjected to high acceleration from drop or vibration. Another mitigation includes software requiring the switch to be closed for a minimum amount of time. For example, when closed it would begin timing and only permanently power-on the device if the switch is closed constantly for 3 seconds, such that instantaneous triggers from drop or vibration would not permanently power-on the device. Another mitigation includes automatically powering-down again to storage mode if a wireless connection (e.g., Bluetooth pairing with a companion device 30) does not occur, so that incidental triggering of the switch, whether in manufacturing, transit, or a user who is not activating the device yet, would only lead to a brief power drain and not permanent powering-on of the device.

Figure 30:
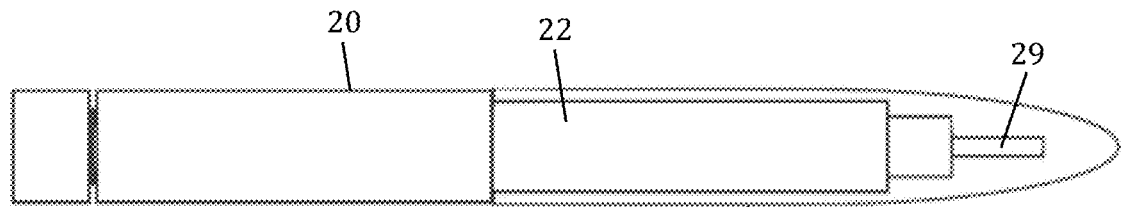
FIGS. 30-32 are block diagrams of example embodiments of the intelligent tracking accessory of FIG. 3 showing battery placement.
Figure 31:
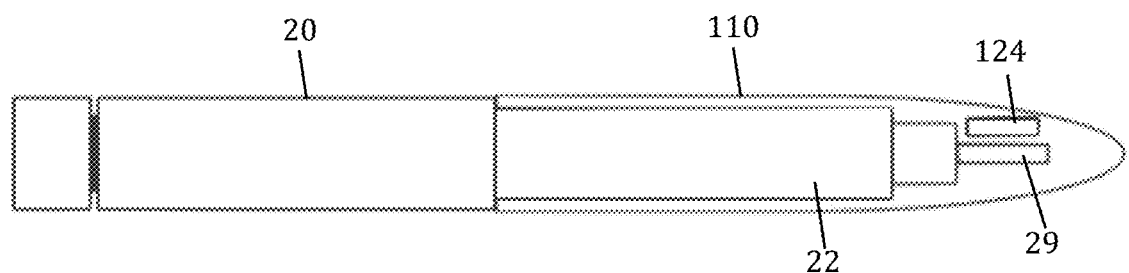
Figure 32:
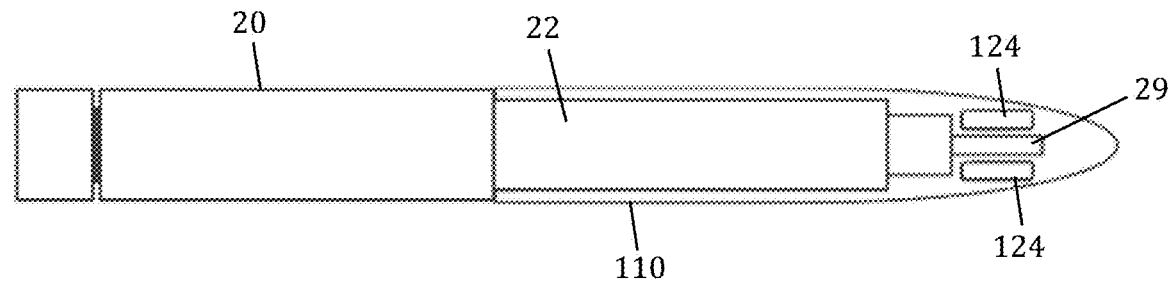

By way of example, FIGS. 30-32 illustrate examples of alternative battery placement configurations according to one embodiment. Typically, injector caps (e.g., cap 110 for an insulin pen 20) are hollow, generally cylindrical, and long enough so that a needle 29 may remain installed when the device is capped. The tip of the needle 29 is generally much smaller diameter than the medicine cartridge 22, so this means there is large empty space surrounding the needle 29, as illustrated by way of example in FIG. 30. In an example embodiment of the smart cap 110, this volume may be utilized with a battery 124, switch, or other circuitry mounted in the location within the overall cap envelope but surrounding the small diameter needle area. FIG. 31 illustrates an example of a smart cap 110 having a single battery 124 placed within the empty volume surrounding the needle 29. FIG. 32 illustrates an example of a smart cap 110 having a battery 124 placed on either side of the needle 29 within the empty volume.

In addition to a smart cap 110 that replaces an injector device's original cap, the smart tracking accessory may take the form of a dock. If the injector is stored within the dock, the dock may detect when the injector is removed and replaced, and may infer that a dose was taken in this time.

The accessory may take the form of a case that stores the injection device, and may detect when the case is opened and closed, or when the injector is removed and replaced. The case may also serve as a tabletop dock than then closes as a case for travel.

The accessory may clip onto the existing injector's cap or main body and detect when the cap is removed via a contact switch or non-contact means such as optical or inductive detection of the pen or cap.

In some embodiments, the system can include a smart medicine delivery pen 20 ("smart pen") or other insulin delivery device that automatically logs doses in a software application 40 resident on the smart pen 20 and/or on a companion device 30 (e.g., a smartphone, smartwatch, or other computing device in wireless communication with the smart pen 20, for example, via a wireless connection).

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A removable tracking device, comprising:
   a cap configured to releasably couple to a distal end portion of a medicine dispensing device, the cap defining an interior cavity between an open proximal end configured to receive the distal end portion of the medicine dispensing device and a closed distal end configured to protect a needle of the medicine dispensing device when the cap is coupled to the distal end portion of the medicine dispensing device;
   an interchangeable coupler adapter configured to enable coupling of the cap to a plurality of medicine dispensing devices of different geometries, the coupler adapter having a first end portion configured to be received within the interior cavity defined by the cap for removably coupling the coupler adapter to the cap and a second end portion defining an axial lumen configured to accommodate the distal end portion of at least one medicine dispensing device of the plurality of medicine dispensing devices of different geometries for removably coupling the distal end portion of the at least one medicine dispensing device to the coupler adapter and the cap;
   a detection switch disposed within the cap and configured to detect:
      removal of the cap from the medicine dispensing device in response to the distal end portion of the medicine dispensing device being removed from the interior cavity of the cap; and
      coupling of the cap to the medicine dispensing device in response to the distal end portion of the medicine dispensing device being received within the interior cavity of the cap;
   a processor disposed within the cap and configured to process at least one of time data or dose data corresponding to a dose of medicine dispensed from the medicine dispensing device; and
   a storage module disposed within the cap and storing instructions which, when executed by the processor, cause performance of:
      determining whether an activation event occurred within a predetermined period of time that includes comparing the time of the activation event to the predetermined period of time, and upon a determination that the dose of medicine was dispensed within the predetermined period of time, identifying the dispensing of the dose of medicine as a safe dosing condition, and upon a determination that the activation event occurred outside of the predetermined period of time, identifying the activation event as an unsafe dosing condition; and
      displaying, on a user interface of the cap, a first visual indication to indicate an identified safe dosing condition and a second visual indication to indicate an identified unsafe dosing condition, the second visual indication being different than the first visual indication.

2. The removable tracking device of claim 1, wherein upon identifying the activation event as a safe dosing condition, the instructions, when executed by the processor, further cause performance of logging the occurrence of a therapeutic dose event upon expiration of a predetermined period of time measured from the onset of the activation event.

3. The removable tracking device of claim 2, wherein upon a coupling of the cap to the medicine dispensing device, as detected by the detection switch, before the expiration of the predetermined period of time, the instructions, when executed by the processor, further cause performance of:
   aborting logging of the occurrence of a therapeutic dose event; and
   logging the occurrence of a status check event.

4. The removable tracking device of claim 1, wherein the predetermined period of time comprises a time threshold corresponding to the amount of time a user ordinarily takes to administer a dose of medicine.

5. The removable tracking device of claim 1, wherein the user interface of the cap includes first and second visual indicators.

6. The removable tracking device of claim 5, wherein the first and second visual indicators each comprise an LED.

7. The removable tracking device of claim 6, wherein the first visual indication comprises a light emission of a first color and the second visual indication comprises a light emission of a second color.

8. The removable tracking device of claim 5, wherein the first and second visual indicators are configured to illuminate in one or more illumination states, the illumination states comprising:
    a first illumination state wherein neither the first nor the second visual indicator is illuminated, indicating that the removable tracking device is not working properly;
    a second illumination state wherein the first visual indicator is illuminated and the second visual indicator is not illuminated, indicating the safe dosing condition;
    a third illumination state wherein the first visual indicator is not illuminated and the second visual indicator is illuminated, indicating the unsafe dosing condition; and
    a fourth illumination state wherein the first and second visual indicators are both illuminated, indicating at least one of a low battery alert, a high temperature alert, a low temperature alert, or an instruction to change a medicine dose amount.

9. The removable tracking device of claim 5, wherein the first visual indicator is operable to activate only within a predetermined time period after the activation event, and wherein the second visual indicator is operable to activate for a time period based on a calculation when it is safe for the user to inject a dose of the medicine.

10. The removable tracking device of claim 5, wherein the first visual indicator is operable to emit light at one or more of a bright illumination or a high duty cycle relative to the second visual indicator.

11. The removable tracking device of claim 1, wherein the dose data includes at least one of dose schedule data or dose log data.

12. The removable tracking device of claim 1, wherein the distal end portion of the medicine dispensing device includes the needle and a needle hub coupled to the needle.

13. The removable tracking device of claim 1, wherein the cap includes a communications module configured to communicate with at least one of a smart phone, a tablet computer, a smart watch, smart glasses, a portable computing device or a wearable computing device.

14. The removable tracking device of claim 1, wherein the medicine dispensing device includes a cartridge containing liquid medication and an injection mechanism configured to enable dispensing of the liquid medication from the cartridge.

15. The removable tracking device of claim 1, wherein the medicine dispensing device includes a sealable container having a detachable lid for containing oral medication within the sealable container.

16. A smart cap for a medicine dispensing device, the smart cap comprising:
    a housing configured to releasably couple to a distal end portion of a medicine dispensing device, the housing defining an interior cavity between an open proximal end configured to receive the distal end portion of the medicine dispensing device and a closed distal end configured to protect a needle of the medicine dispensing device when the housing is coupled to the distal end portion of the medicine dispensing device;
    an interchangeable coupler adapter configured to enable coupling of the housing to a plurality of medicine dispensing devices of different geometries, the coupler adapter having a first end portion configured to be received within the interior cavity defined by the housing for removably coupling the coupler adapter to the housing and a second end portion defining an axial lumen configured to accommodate the distal end portion of at least one medicine dispensing device of the plurality of medicine dispensing devices of different geometries for removably coupling the distal end portion of the medicine dispensing device to the coupler adapter and the housing;
    a detection switch disposed within the housing and configured to be actuated by the distal end portion of the medicine dispensing device upon receipt of the distal end portion within the interior cavity and upon removal of the distal end portion from within the interior cavity for detecting whether the distal end portion of the medicine dispensing device is disposed in or removed from the interior cavity of the housing;
    a processor disposed within the housing;
    a memory disposed within the housing and storing instructions which, when executed by the processor, cause performance of:
        determining, in response to actuation of the detection switch caused by removal of the distal end portion of the medicine dispensing device from the interior cavity of the housing, whether a predetermined period of time has elapsed since the medicine dispensing device dispensed a dose of medicine;
        identifying one of a safe dosing condition or an unsafe dosing condition based on the determination of whether the predetermined period of time has elapsed; and
        displaying, on a user interface of the housing, at least one visual indication to indicate the safe dosing condition or the unsafe dosing condition.

17. The smart cap of claim 16, wherein the instructions, when executed by the processor, further cause performance of:
    logging, in response to identification of a safe dosing condition, a medicine dose dispensing event associated with the medicine dispensing device if a predetermined period of time has elapsed since the detection switch was actuated by removal of the distal end portion of the medicine dispensing device from within the interior cavity of the housing.

18. The smart cap of claim 16, wherein the instructions, when executed by the processor, further cause performance of:
    preventing, in response to identification of a safe dosing condition, logging of a medicine dose dispensing event associated with the medicine dispensing device if actuation of the detection switch caused by receipt of the distal end portion of the medicine dispensing device within the interior cavity of the housing occurs within a predetermined period of time since the detection switch was actuated by removal of the distal end portion of the medicine dispensing device from within the interior cavity of the housing.

19. The smart cap of claim 16, wherein the instructions, when executed by the processor, further cause performance of:
preventing, in response to identification of an unsafe dosing condition, logging of a medicine dose dispensing event associated with the medicine dispensing device until the detection switch is actuated by receipt of the distal end portion of the medicine dispensing device within the interior cavity of the housing.

20. A smart cap for a medicine dispensing device, comprising:
a cap housing configured to releasably couple to a distal end portion of a medicine dispensing device, the cap housing defining an interior cavity between an open proximal end configured to receive the distal end portion of the medicine dispensing device and a closed distal end configured to protect a needle of the medicine dispensing device when the cap housing is coupled to the distal end portion of the medicine dispensing device; and
an interchangeable coupler adapter configured to enable coupling of the cap housing to a plurality of medicine dispensing devices of different geometries, the coupler adapter having a first end portion configured to be received within the interior cavity defined by the cap housing for removably coupling the coupler adapter to the cap housing and a second end portion defining an axial lumen configured to accommodate the distal end portion of at least one medicine dispensing device of the plurality of medicine dispensing devices for removably coupling the distal end portion of the medicine dispensing device to the coupler adapter and the cap housing.

21. The smart cap according to claim 20, wherein the cap housing includes a communications module configured to communicate with at least one of a smart phone, a tablet computer, a smart watch, smart glasses, a portable computing device or a wearable computing device.

22. The smart cap according to claim 20, wherein the cap housing includes a switch configured to detect coupling of the cap housing to the medicine dispensing device and removal of the cap housing from the medicine dispensing device.

23. The smart cap according to claim 20, wherein the cap housing includes a processor configured to process at least one of time data or dose data corresponding to a dose of medicine dispensed from the medicine dispensing device.

24. The smart cap according to claim 20, wherein the coupler adapter includes a plurality of arms configured to:
expand radially outward to accommodate the distal end portion of the medicine dispensing device within the axial lumen during insertion of the distal end portion of the medicine dispensing device into the axial lumen; and
apply a radial inward force on the distal end portion of the medicine dispensing device when the distal end portion of the medicine dispensing device is coupled to the coupler adapter.

* * * * *